(12) United States Patent
Sarkar et al.

(10) Patent No.: US 10,542,887 B2
(45) Date of Patent: Jan. 28, 2020

(54) HEART FAILURE MONITORING

(75) Inventors: Shantanu Sarkar, Roseville, MN (US); Jodi L. Redemske, Fridley, MN (US); Eduardo N. Warman, Maple Grove, MN (US); Douglas A. Hettrick, Andover, MN (US); Kevin T. Ousdigian, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 2435 days.

(21) Appl. No.: 13/436,408

(22) Filed: Mar. 30, 2012

(65) Prior Publication Data

US 2012/0253207 A1 Oct. 4, 2012

Related U.S. Application Data

(60) Provisional application No. 61/470,647, filed on Apr. 1, 2011.

(51) Int. Cl.
*A61B 5/02* (2006.01)
*A61B 5/00* (2006.01)

(52) U.S. Cl.
CPC .................. *A61B 5/0006* (2013.01)

(58) Field of Classification Search
CPC ................................. A61B 5/0205
See application file for complete search history.

(56) References Cited

U.S. PATENT DOCUMENTS

| 4,374,382 A | 2/1983 | Markowitz |
| 4,763,646 A | 8/1988 | Lekholm |

(Continued)

FOREIGN PATENT DOCUMENTS

| WO | 2011/002535 A1 | 6/2011 |
| WO | 2011/126823 A1 | 10/2011 |

OTHER PUBLICATIONS

Whellan, et al. "Combined heart failure device diagnostics identify patients at higher risk of subsequent heart failure hospitalizations: results from PARTNERS HF (Program to Access and Review Trending Information and Evaluate Correlation to Symptoms in Patients With Heart Failure) study." J Am Coll Cardiol. Apr. 27, 2010;55(17):1803-10.*

(Continued)

*Primary Examiner* — Eric J Messersmith

(57) ABSTRACT

Techniques for transmitting diagnostic information stored in an implantable medical device (IMD) based on patient hospitalization are described. For example, the IMD may transmit higher resolution diagnostic information to a clinician and/or an external device during a hospitalization period to aid the clinician in evaluating heart failure treatment and when discharge is proper. This higher resolution diagnostic information may include one or more patient metrics automatically generated and transmitted by the IMD at least once every two hours. During a post-hospitalization period, the IMD may transmit lower resolution diagnostic information to a clinician that indicates a risk level of re-hospitalization. The lower resolution diagnostic information may include the risk level and/or patient metrics once a day, for example. In this manner, the IMD transmitted diagnostic information may be tailored to the specific heart failure monitoring needed by the patient.

22 Claims, 16 Drawing Sheets

(56) References Cited

U.S. PATENT DOCUMENTS

| | | |
|---|---|---|
| 5,117,824 A | 6/1992 | Keimel et al. |
| 5,545,186 A | 8/1996 | Olson et al. |
| 5,755,736 A | 5/1998 | Gillberg et al. |
| 6,115,622 A | 9/2000 | Minoz |
| 6,393,316 B1 | 5/2002 | Gillberg et al. |
| 6,477,406 B1 | 11/2002 | Turcott |
| 6,527,729 B1* | 3/2003 | Turcott ............ 600/528 |
| 6,643,548 B1 | 11/2003 | Mai et al. |
| 7,174,203 B2 | 2/2007 | Arand et al. |
| 7,209,786 B2 | 4/2007 | Brockway et al. |
| 7,218,966 B2 | 5/2007 | Haefner |
| 7,433,853 B2* | 10/2008 | Brockway ............ A61B 5/0002 706/45 |
| 8,140,156 B2 | 3/2012 | Zhang et al. |
| 2001/0039437 A1* | 11/2001 | Taepke et al. ............ 607/27 |
| 2002/0052539 A1* | 5/2002 | Haller ............ A61B 5/0031 600/300 |
| 2002/0123672 A1* | 9/2002 | Christophersom ............ A61N 1/37282 600/300 |
| 2003/0060723 A1 | 3/2003 | Joo et al. |
| 2004/0127792 A1 | 7/2004 | Siejko et al. |
| 2005/0010257 A1 | 1/2005 | Lincoln et al. |
| 2005/0113647 A1 | 5/2005 | Lee et al. |
| 2006/0241702 A1 | 10/2006 | Gillberg |
| 2006/0264776 A1 | 11/2006 | Stahmann et al. |
| 2006/0282000 A1 | 12/2006 | Zhang et al. |
| 2007/0142866 A1 | 6/2007 | Li et al. |
| 2007/0149890 A1 | 6/2007 | Li et al. |
| 2007/0239218 A1 | 10/2007 | Carlson et al. |
| 2008/0125820 A1* | 5/2008 | Stahmann ............ A61B 5/0031 607/4 |
| 2008/0177191 A1 | 7/2008 | Patangay et al. |
| 2008/0228090 A1* | 9/2008 | Wariar ............ A61B 5/0031 600/508 |
| 2009/0125328 A1* | 5/2009 | Nevins ............ 705/3 |
| 2010/0030292 A1 | 2/2010 | Sarkar et al. |
| 2010/0185109 A1 | 7/2010 | Zhang et al. |
| 2011/0040713 A1* | 2/2011 | Colman et al. ............ 706/16 |
| 2012/0157797 A1* | 6/2012 | Zhang et al. ............ 600/301 |
| 2013/0197381 A1* | 8/2013 | Charlton ............ A61B 5/686 600/523 |

OTHER PUBLICATIONS

International Preliminary Report on Patentability for corresponding International Application No. PCT/US2012/031708, dated Oct. 1, 2013, 6 pages.

Notification Concerning Transmittal of International Preliminary Report on Patentability for corresponding International Application No. PCT/US2012/031708, dated Oct. 10, 2013, 1 page.

Office Action from U.S. Appl. No. 12/495,204, dated Sep. 26, 2011, 7 pp.

Response to Office Action dated Sep. 26, 2011, from U.S. Appl. No. 12/495,204, filed Jan. 2012, 12 pp.

Notice of Allowance for U.S. Appl. No. 12/495,204, dated Feb. 3, 2012, 9 pp.

International Search Report and Written Opinion of PCT/US2012/031708, dated Jul. 27, 2012, 10 pp.

* cited by examiner

HEART FAILURE MONITORING

This application claims the benefit of U.S. Provisional Application Ser. No. 61/470,647, filed Apr. 1, 2011, the entire content of which is incorporated herein by reference.

TECHNICAL FIELD

The invention relates to medical devices, and, more particularly, to medical devices that monitor cardiac health.

BACKGROUND

Heart failure is a condition affecting thousands of people worldwide. Essentially, congestive heart failure occurs when the heart is unable to pump blood at an adequate rate in response to the filling pressure. This condition may result in congestion in the tissue, peripheral edema, pulmonary edema, and even shortness of breath. When heart failure is severe, it can even lead to patient death.

Although heart failure treatments may include electrical stimulation therapy and drug therapy, drug therapy has been the more effective treatment for most patients. For example, patients suffering from or at risk for heart failure may be treated with diuretic agents and/or angiotensin converting enzyme inhibitors. In addition, patients may be treated with nitroglycerin to reduce the symptoms of heart failure. Even though treatments are available, patients with other cardiac conditions may be at greater risk of severe complications with the conditions of heart failure.

SUMMARY

Generally, this disclosure describes techniques for transmitting diagnostic information stored in an implantable medical device (IMD) that is indicative of heart failure risk. An implantable medical device (IMD), e.g., a pacemaker, cardioverter and/or defibrillator, or a monitor that does not provide therapy, may automatically generate and store patient data. The patient data may include therapy use statistics (e.g., pacing or shocks), thoracic impedance, heart rate, heart rate variability, patient activity, atrial arrhythmias, cardiac resynchronization therapy percentages, and other patient metrics. During a hospitalization period of the patient, higher resolution diagnostic information based on one or more patient metrics may be transmitted to a user to aid the evaluation of heart failure treatment. This higher resolution diagnostic information may include raw data collected to determine values for the patient metrics. The higher resolution diagnostic information may be transmitted to the user at least several times a day, and may be used to determine when hospital discharge is proper.

During a non-hospitalization period of the patient, lower resolution diagnostic information based on the patient metrics may be transmitted to the user, which may be used to determine a risk level of the patient being admitted to the hospital due to heart failure. For example, during a post-hospitalization period of the patient, lower resolution diagnostic information based on the patient metrics may be transmitted to the user, which may be used to determine a risk level of the patient being re-admitted to the hospital due to heart failure. A clinician may receive the lower resolution diagnostic information remotely and tailor further heart failure treatment based on the information. In some examples, the clinician or clinic may receive the lower resolution diagnostic information on a daily basis from several patients. In this manner, the heart failure risk level may help the clinician or clinic triage patient care and assist those patients at highest risk for hospitalization first.

In one example, the disclosure describes a method that includes storing a plurality of automatically detected patient metrics within an implantable medical device of a patient, transmitting higher resolution diagnostic information during a hospitalization period of the patient, wherein the higher resolution diagnostic information is based on at least one of the plurality of patient metrics and indicative of heart failure, and transmitting lower resolution diagnostic information during a post-hospitalization period of the patient, wherein the lower resolution diagnostic information is based on the plurality of patient metrics and indicative of a potential re-hospitalization period due to heart failure.

In another example, the disclosure describes an implantable medical device that includes a memory configured to store a plurality of automatically detected patient metrics, a metric detection module configured to generate higher resolution diagnostic information based on at least one of the plurality of patient metrics and indicative of heart failure and generate lower resolution diagnostic information based on the plurality of patient metrics and indicative of a potential re-hospitalization period due to heart failure, and a telemetry module configured to transmit the higher resolution diagnostic information during a hospitalization period of the patient and lower resolution diagnostic information during a post-hospitalization period of the patient.

In another example, the disclosure describes a system including means for storing a plurality of automatically detected patient metrics within an implantable medical device of a patient and means for transmitting information. The means for transmitting information includes means for transmitting higher resolution diagnostic information during a hospitalization period of the patient, the higher resolution diagnostic information is based on at least one of the plurality of patient metrics and indicative of heart failure, the means for transmitting information comprises means for transmitting lower resolution diagnostic information during a post-hospitalization period of the patient, and the lower resolution diagnostic information is based on the plurality of patient metrics and indicative of a potential re-hospitalization period due to heart failure.

The details of one or more examples are set forth in the accompanying drawings and the description below. Other features, objects, and advantages will be apparent from the description and drawings, and from the claims.

DETAILED DESCRIPTION

Figure 1:
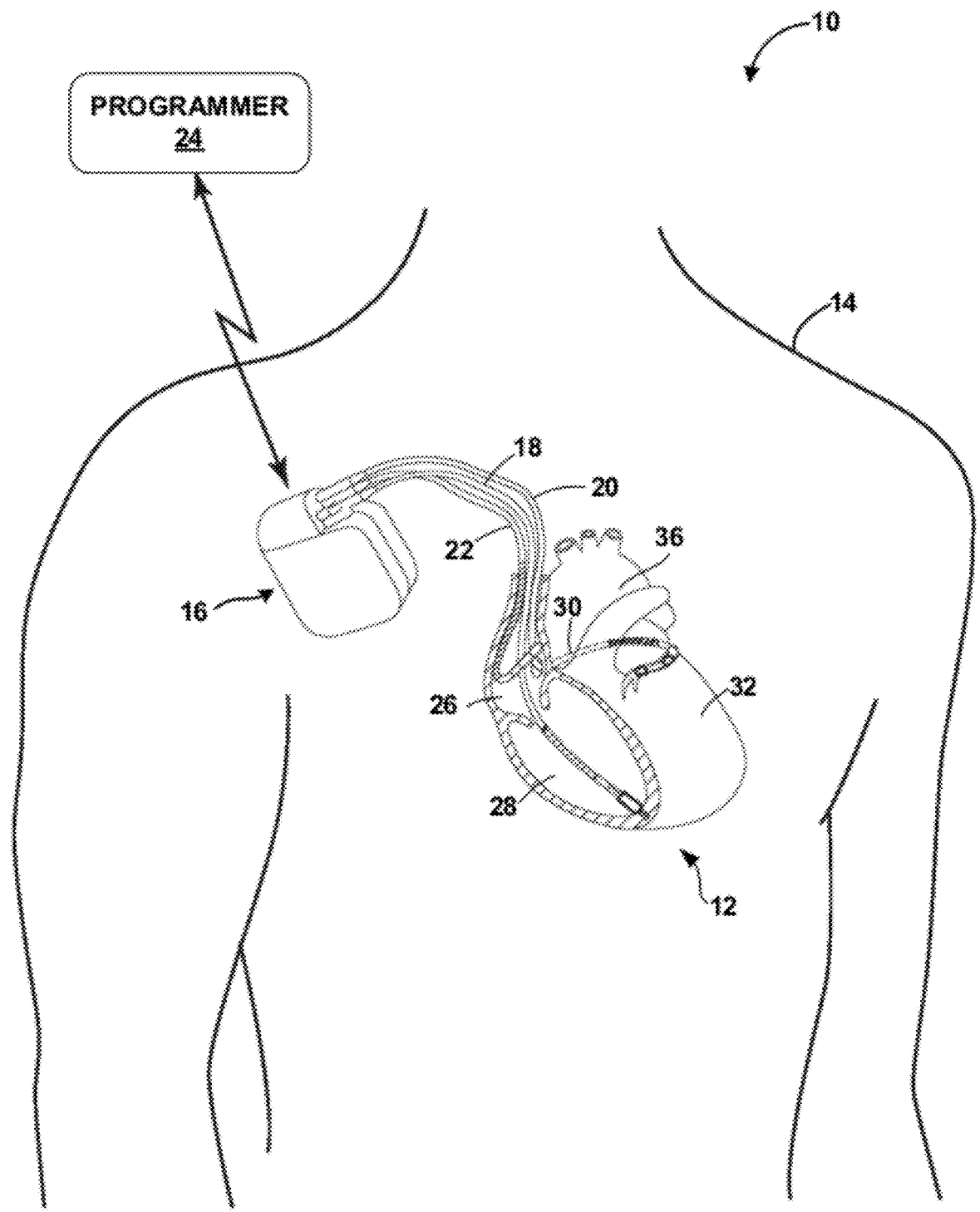
FIG. 1 is a conceptual drawing illustrating an example system configured to transmit diagnostic information indicative of heart failure that includes an implantable medical device (IMD) coupled to implantable medical leads.

This disclosure describes techniques for transmitting diagnostic information stored in an implantable medical device (IMD) that is indicative of heart failure. Congestive heart failure may occur gradually over time due to heart disease, patient inactivity, cardiac arrhythmias, hypertension, and other conditions. Often, however, a relatively rapid worsening of the patient's condition, e.g., a decompensation, precipitates hospitalization and, in some cases, death.

Although health care professionals may monitor patients for potential risk of worsening heart failure during a hospitalization period, e.g., decompensation, valuable information generated by an IMD of the patient may not be available to the health care professionals during the hospitalization period. Additionally, invasive hemodynamic monitoring of pulmonary capillary wedge pressure during hospitalization is rarely performed. Thus, clinicians may have few objective patient data by which to evaluate patient health during hospitalization. It also may not be possible to continually monitor patients before hospitalization or during a post-hospitalization period.

Certain conditions may be automatically monitored and used to create a heart failure risk level that a clinician may review periodically, or that may be automatically transmitted to a clinician when the heart failure risk level indicates that the patient is at an increased risk for re-hospitalization due to an increased possibility of a heart failure event. Using the risk level, a clinician or other healthcare professional may alter or titrate the treatment of the patient to prevent further deterioration and admission to the hospital.

An implantable medical device (IMD), e.g., a pacemaker, cardioverter and/or defibrillator, or a monitor that does not provide therapy, may automatically generate and store patient data regarding patient metrics. The patient metrics may include, as examples, therapy use statistics (e.g., pacing or shocks), thoracic impedance, heart rate, heart rate variability, patient activity, and a percentage of time receiving cardiac resynchronization therapy. Other example patient metrics include weight, blood pressure, respiration rate, sleep apnea burden (which may be derived from respiration rate), temperature, ischemia burden, the occurrence, frequency or duration cardiac events, and sensed cardiac intervals (e.g., heart rate or Q-T intervals). Examples of cardiac events may include atrial and ventricular tachyarrhythmias. Another example patient metric is the ventricular rate during atrial fibrillation. The concentration or levels of various substances, such as blood glucose, hematocrit, troponin and/or brain natriuretic peptide (BNP) levels, within the patient may also be used as one or more patient metrics.

The IMD may provide diagnostic information to one or more users via one or more devices, such as IMD programmers or other computing devices. The diagnostic information may be related to, generated from, or may even include the one or more patient metrics. The diagnostic information may include, as examples, values of the patient metrics and raw data used to derive the values of the patient metrics.

The IMD may provide different resolutions of such diagnostic information dependent on whether or not the patient is hospitalized. During a hospitalization period of the patient, higher resolution diagnostic information based on one or more patient metrics may be transmitted to a user to aid the evaluation of heart failure treatment and to determine when hospital discharge is proper. The resolution of the data may refer to how often the data is transmitted, with higher resolution data being transferred more frequently. The resolution of data may also refer to whether the data includes raw values of measured patient metrics, such as thoracic impedance, or values derived from such raw values, with raw values being of higher resolution than derived values. In one example, higher resolution diagnostic information may be in the form of raw data, e.g., a thoracic impedance, that is transmitted at least several times a day. Higher resolution diagnostic information may include frequently collected patient metrics such that the resolution may allow for relatively continuous monitoring of the patient. The IMD may provide higher resolution diagnostic information not readily available from sources other than the IMD, e.g., other sources may include external bed-side monitors, laboratory tests, or various imaging modalities.

During a non-hospitalization period of the patient, e.g., a post-hospitalization period of the patient, lower resolution diagnostic information based on the patient metrics may be transmitted to the user. This lower resolution diagnostic information may take the form of a risk level of the patient being admitted to the hospital due to heart failure, e.g., readmitted to the hospital within the next thirty days, for example. The lower resolution diagnostic information may be generated from patient metrics detected over a predetermined period, e.g., the most recent seven days post-hospitalization.

The risk level may be considered "lower resolution" because the risk level may be transmitted from the IMD at a lesser frequency than during the hospitalization period, e.g., once a day, and/or not include values of one or more of the stored patient metrics. In other words, lower resolution diagnostic information may be a more generalized indication of the overall risk or probability that the patient is at a high risk of being hospitalized due to heart failure. In comparison, the higher resolution diagnostic information may include metrics detected at a greater frequency and/or metrics with greater detail than the lower resolution diagnostic information. A clinician may receive the lower resolution diagnostic information remotely, and titrate further heart failure treatment based on the information. With the transmission of either higher or lower resolution diagnostic information, the IMD may automatically transmit the information or transmit the information in response to an interrogation request from the user.

In some examples, the lower resolution diagnostic information may be transmitted from a plurality of IMDs implanted in different patients to healthcare professionals through different methods and different channels. In this manner, for example, the heart failure risk level may help the healthcare professionals to triage patient care and first assist those patients at highest risk for hospitalization. A remote computing device may receive the remotely transmitted lower resolution diagnostic information and present each patient ranked according to the risk levels, e.g., from highest to lowest risk levels. Transmission from each IMD may be completed on a daily basis, for example, either automatically or in response to a remote or local interrogation request.

As described herein, the IMD may generate diagnostic information that is based on one or more patient metrics and specific to the current treatment state of the patient. In this manner, the diagnostic information may vary based on the type of information desired by a healthcare professional. For example, the IMD may be capable of transmitting values of individual patient metrics during hospitalization and a re-hospitalization risk level after discharge from the hospital. In other examples, the IMD may transmit previously stored patient metrics or risk levels to a healthcare professional to aid in the determination of whether the patient should be admitted to a hospital. Therefore, an IMD may be a flexible diagnostic tool usable within or outside of a hospital setting.

FIG. 1 is a conceptual drawing illustrating an example system 10 configured to transmit diagnostic information indicative of heart failure of patient 14. In the example of FIG. 1, system 10 includes IMD 16, which is coupled to leads 18, 20, and 22 and programmer 24. IMD 16 may be, for example, an implantable pacemaker, cardioverter, and/or defibrillator that provides electrical signals to heart 12 via electrodes coupled to one or more of leads 18, 20, and 22. Patient 14 is ordinarily, but not necessarily a human patient.

Although an implantable medical device and delivery of electrical stimulation to heart 12 are described herein as examples, the techniques for detecting patient metrics and transmitting high and lower resolution diagnostic information of this disclosure may be applicable to other medical devices and/or other therapies. In general, the techniques described in this disclosure may be implemented by any medical device, e.g., implantable or external, that senses a signal indicative of cardiac activity, patient 14 activity, and/or fluid volume within patient 14. As one alternative example, the techniques described herein may be implemented in an external cardiac monitor that generates electrograms of heart 12 and detects thoracic fluid volumes, respiration, and/or cardiovascular pressure of patient 14.

In the example of FIG. 1, leads 18, 20, 22 extend into the heart 12 of patient 14 to sense electrical activity of heart 12 and/or deliver electrical stimulation to heart 12. Leads 18, 20, and 22 may also be used to detect a thoracic impedance indicative of fluid volume in patient 14, respiration rates, sleep apnea, or other patient metrics. Respiration metrics, e.g., respiration rates, tidal volume, and sleep apnea, may also be detectable via an electrogram, e.g., based on a signal component in a cardiac electrogram that is associated with respiration. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, system 10 may additionally or alternatively include one or more leads or lead segments (not shown in FIG. 1) that deploy one or more electrodes within the vena cava, or other veins. Furthermore, in some examples, system 10 may additionally or alternatively include temporary or permanent epicardial or subcutaneous leads with electrodes implanted outside of heart 12, instead of or in addition to transvenous, intracardiac leads 18, 20 and 22. Such leads may be used for one or more of cardiac sensing, pacing, or cardioversion/defibrillation. For example, these electrodes may allow alternative electrical sensing configurations that provide improved or supplemental sensing in some patients. In other examples, these other leads may be used to detect intrathoracic impedance as a patient metric for identifying a heart failure risk or fluid retention levels.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may detect arrhythmia of heart 12, such as tachycardia or fibrillation of the atria 26 and 36 and/or ventricles 28 and 32, and may also provide defibrillation therapy and/or cardioversion therapy via electrodes located on at least one of the leads 18, 20, 22. In some examples, IMD 16 may be programmed to deliver a progression of therapies, e.g., pulses with increasing energy levels, until a fibrillation of heart 12 is stopped. IMD 16 may detect fibrillation employing one or more fibrillation detection techniques known in the art.

In addition, IMD 16 may monitor the electrical signals of heart 12 for patient metrics stored in IMD 16 and/or used in generating the heart failure risk level. IMD 16 may utilize two of any electrodes carried on leads 18, 20, 22 to generate electrograms of cardiac activity. In some examples, IMD 16 may also use a housing electrode of IMD 16 (not shown) to generate electrograms and monitor cardiac activity. Although these electrograms may be used to monitor heart 12 for potential arrhythmias and other disorders for therapy, the electrograms may also be used to monitor the condition of heart 12. For example, IMD 16 may monitor heart rate (night time and day time), heart rate variability, ventricular or atrial intrinsic pacing rates, indicators of blood flow, or other indicators of the ability of heart 12 to pump blood or the progression of heart failure.

In some examples, IMD 16 may also use any two electrodes of leads 18, 20, and 22 or the housing electrode to sense the intrathoracic impedance of patient 14. As the tissues within the thoracic cavity of patient 14 increase in fluid content, the impedance between two electrodes may also change. For example, the impedance between an RV coil electrode and the housing electrode may be used to monitor changing intrathoracic impedance.

IMD 16 may use this impedance to create a fluid index. As the fluid index increases, more fluid is being retained within patient 14 and heart 12 may be stressed to keep up with moving the greater amount of fluid. Therefore, this fluid index may be a patient metric transmitted in higher resolution diagnostic data or used to generate the heart failure risk level. By monitoring the fluid index in addition to other patient metrics, IMD 16 may be able to reduce the number of false positive heart failure identifications relative to what might occur when monitoring only one or two patient metrics. Furthermore, IMD 16, along with other networked computing devices described herein, may facilitate remote monitoring of patient 14, e.g., monitoring by a health care professional when the patient is not located in a healthcare facility or clinic associated with the health care professional, during a post-hospitalization period. An example system for measuring thoracic impedance and determining a fluid index is described in U.S. Patent Publication No. 2010/0030292 to Sarkar et al., entitled, "DETECTING WORSENING HEART FAILURE BASED ON IMPEDANCE MEASUREMENTS," which published on Feb. 4, 2010 and is incorporated herein by reference in its entirety.

IMD 16 may also communicate with external programmer 24. In some examples, programmer 24 comprises an external device, e.g., a handheld computing device, computer workstation, or networked computing device. Programmer 24 may include a user interface that receives input from a user. In other examples, the user may also interact with programmer 24 remotely via a networked computing device. The user may interact with programmer 24 to communicate with IMD 16. For example, the user may interact with programmer 24 to send an interrogation request and retrieve patient metrics or other diagnostic information from IMD 16. A user may also interact with programmer 24 to program IMD 16, e.g., select values for operational parameters of IMD 16. Although the user is a physician, technician, surgeon, electrophysiologist, or other healthcare professional, the user may be patient 14 in some examples.

For example, the user may use programmer 24 to retrieve information from IMD 16 regarding patient metric data and/or the heart failure risk level. In one example, the patient metric data may be transmitted as higher resolution diagnostic information during a hospitalization period of patient 14. In another example, the heart failure risk level may be transmitted as lower resolution diagnostic information during a post-hospitalization period. Although programmer 24 may retrieve this information after submitting an interrogation request, IMD 16 may push or transmit the heart failure risk level, for example, if the heart failure risk level indicates a change in patient treatment is necessary. For example, the risk level may be determined based on a predetermined number of patient metrics exceeding their representative thresholds or a weighted score for each of the patient metrics for exceeding one or more thresholds. Additionally or alternatively, the risk level may be determined by a Bayesian Belief Network, or other probability technique, using the values or stratified states of each automatically detected patient metric.

Although IMD 16 may generate the heart failure risk level, IMD 16 may transmit the patient metric data and programmer 24 may generate the heart failure risk level in other examples. Programmer 24 may present an alert to the user with the higher or lower resolution diagnostic information, e.g., the heart failure risk level and/or other patient metric data. The patient metric data may include intracardiac or intravascular pressure, activity, posture, respiration, or thoracic impedance.

As another example, the user may use programmer 24 to retrieve information from IMD 16 regarding the performance or integrity of IMD 16 or other components of system 10, such as leads 18, 20 and 22, or a power source of IMD 16. In some examples, any of this information may be presented to the user as an alert (e.g., a notification or instruction). Further, alerts may be pushed from IMD 16 to facilitate alert delivery whenever programmer 24 is detectable by IMD 16. IMD 16 may wirelessly transmit alerts, or other higher or lower resolution diagnostic information, to facilitate immediate notification of the heart failure condition.

Programmer 24 may also allow the user to define how IMD 16 senses, detects, and manages each of the patient metrics. For example, the user may define the frequency of sampling or the evaluation window used to monitor the patient metrics. In addition, the user may use programmer 24 to set each metric threshold used to monitor the status of each patient metric. The metric thresholds may be used to determine when each of the patient metrics has reached a magnitude indicative of being at risk for heart failure. In some examples, when a patient metric exceeds its respective metric threshold, the metric may be counted in the predetermined number used to create the heart failure risk level. For example, if two of the eight patient metrics exceed their thresholds, the heart failure risk level may be described as a high risk level for patient 14 to be hospitalized, e.g., re-hospitalized, within thirty days. This heart failure risk level may indicate that patient 14 is at an increased risk of heart failure if the predetermined number of patient metrics exceeding their respective thresholds is one or more.

The risk level may be a predetermined number that is set to different values for patients of differing age, weight, cardiac condition, or any number of other risk factors. In other examples, the predetermined number may be set to a different number or a risk level percentage (fraction). In this manner, the predetermined number may represent a preset fraction of unweighted or weighted metrics exceeding a threshold with respect to the total number of monitored metrics. Programmer 24 may be used to set this predetermined number or any other factors used to generate and interpret the heart failure risk level.

In other examples, the risk level may be determined by the sum, average, or other combination of weighted scores for each of the patient metrics. Each patient metric may have one or more metric-specific thresholds that stratify the state of the metric. Since some states or metrics may be more indicative of the risk of re-hospitalization, these states and/or metrics may provide a greater contribution to the determined risk level. For example, a high risk state for intrathoracic impedance may have a weighted score that is double that of a high risk state for patient inactivity. In other words, intrathoracic impedance may be a greater risk factor to the patient than patient inactivity. Alternatively, a probability analysis may be performed on some or all of the patient metrics to determine the probability that patient 14 will be re-hospitalized for heart failure. For example, a Bayesian Belief Network may be applied to the values of the patient metrics to determine the risk level, e.g., the probability, that patient 14 will be re-admitted to the hospital for heart failure.

In some examples, one or more patient metrics may be collected or detected outside of IMD 16. Patient metrics collected outside of IMD 16 may be referred to as "non-device metrics." These non-device metrics may be useful for some patients in determining the heart failure risk level before hospitalization, during hospitalization, and/or during the post-hospitalization period. These non-device metrics may be collected, e.g., received via patient input or electronic transmission from another device, and may be analyzed similar to any other patient metrics described herein. Example non-device metrics may include patient weight, medication compliance, consumed food, liquid intake, activity durations, pain levels, pain locations, urinary or fecal voiding events, or any other non-device metrics that may describe or otherwise characterize the health of patient 14.

IMD 16 and programmer 24 may communicate via wireless communication using any techniques known in the art. Examples of communication techniques may include, for example, radiofrequency (RF) telemetry, but other communication techniques such as magnetic coupling are also contemplated. In some examples, programmer 24 may include a programming head that may be placed proximate to the body of the patient near the IMD 16 implant site in order to improve the quality or security of communication between IMD 16 and programmer 24.

IMD 16 may automatically detect each of the patient metrics and store them within the IMD for later transmission. During a hospitalization period of patient 14, IMD 16 may continue to detect each of the patient metrics, and transmit higher resolution diagnostic information to a user, e.g., a clinician or other health care professional. The higher resolution diagnostic information may be based on at least one of the plurality of patient metrics detected during the hospitalization period, and the higher resolution diagnostic information may also be indicative of heart failure. During a post-hospitalization period of patient 14, IMD 16 may continue to detect each of the patient metrics, and transmit lower resolution diagnostic information to the user. The lower resolution diagnostic information may be based on the plurality of patient metrics collected during the post-hospitalization period, and be indicative of a potential re-hospitalization due to heart failure.

Generally, the higher resolution diagnostic information includes metrics detected at a greater frequency and/or metrics with greater detail than the lower resolution diagnostic information. For example, the higher resolution diagnostic information may include values of at least one patient metric, or other raw data, detected at least once every two hours or on-demand during the hospitalization period. In other examples, the higher resolution diagnostic information may include metrics detected at other frequencies, e.g., once every four hours, once every hour, or once every ten minutes. In some examples, higher resolution diagnostic information may include values collected for a fixed period of time, e.g., one day, seven days, or a month.

During the hospitalization period, higher resolution diagnostic information may be presented to and interpreted by a clinician to better treat patient 14. In some examples, the higher resolution diagnostic information may used by the clinician to determine when to discharge patient 14 from the hospital, i.e., end the hospitalization period. For example, the clinician may use a thoracic impedance value from the higher resolution diagnostic information to identify when diuretics given to patient 14 have reduced fluid retention to a less critical level.

As described herein, IMD 16 automatically detects a plurality of patient metrics from patient 14. These patient metrics may alone, or in combination, be indicative of heart failure of patient 14. The patient metrics may include, as examples, thoracic impedance, heart rate variability, the number, frequency or duration of atrial fibrillation after cardioversion therapy, ventricular rate during persistent atrial fibrillation, night heart rate, or any other metrics detectable from patient 14 or based on the treatment of patient 14. One or more of these patient metrics may be used by the clinician to determine when to discharge patient 14 from the hospital and begin the post-hospitalization period. For example, increases in thoracic fluid impedance, increases in heart rate variability, a lack of atrial fibrillation after cardioversion therapy, a stable ventricular rate during persistent atrial fibrillation, or a stable night heart rate may be indications that the patient is at a lesser risk of heart failure and may be discharged from the hospital.

Generally, lower resolution diagnostic information may include patient metric values detected with lesser frequency than the higher resolution diagnostic information and/or generalized information instead of specific measured values of the patient metric. For example, the lower resolution diagnostic information may include a risk level that indicates the likelihood that patient 14 will be admitted to the hospital, e.g., re-admitted to the hospital after an admission to the hospital for heart failure. The likelihood may be a risk that patient 14 will be hospitalized within a predetermined time period, e.g., 30 days. In one example, the risk level may be generalized into different categories, e.g., high risk, medium risk, and low risk. In other examples, the risk level may be numerical, e.g., to more precisely define the risk of heart failure or admission for patient 14. A clinician may select how the lower resolution diagnostic information may be determined. In other examples, an elevated risk level, e.g., a high or medium risk of heart failure, of the lower resolution diagnostic information may trigger the generation and delivery of higher resolution diagnostic information.

One example technique for determining a risk level for the lower resolution diagnostic information may include using a metric-specific threshold for each of the patient metrics. IMD 16 may compare each of the plurality of automatically detected patient metrics to one of a plurality of metric-specific thresholds. A heart failure risk level may be automatically generated by IMD 16 based on the comparisons. The risk level may be indicative of the potential for re-hospitalization for heart failure within period after a heart failure hospitalization event when a predetermined number of the automatically detected patient metrics each exceed the respective one of the plurality of metric-specific thresholds. In other words, the number of patient metrics that exceed their respective metric-specific threshold may determine the severity of the risk level.

As one example, the heart failure risk level may indicate a high risk of hospitalization when a predetermined number of the plurality of automatically detected patient metrics, such as two or more automatically detected patient metrics, each exceed their respective metric-specific threshold. As another example, the heart failure risk level may indicate a medium risk of hospitalization when a predetermined number of the plurality of automatically detected patient metrics, such as only one automatically detected patient metric, exceeds its respective metric-specific threshold. In an additional example, the heart failure risk level may indicate a low risk of hospitalization when none of the plurality of automatically detected patient metrics exceeds their respective metric-specific thresholds.

Although IMD 16 may automatically detect eight different patient metrics in some examples, IMD 16 may detect more or less patient metrics in other examples. For example, the patient metrics may include two or more of a thoracic fluid index, an atrial fibrillation duration, a ventricular contraction rate during atrial fibrillation, a patient activity, a nighttime heart rate, a heart rate variability, a cardiac resynchronization therapy (CRT) percentage (e.g., the percentage of cardiac cycles for which cardiac resynchronization pacing was provided), or the occurrence of or number of therapeutic electrical shocks. The metric-specific thresholds may include at least two of a thoracic fluid index threshold of approximately 60, an atrial fibrillation duration threshold of approximately 6 hours, a ventricular contraction rate threshold approximately equal to 90 beats per minute for 24 hours, a patient activity threshold approximately equal to 1 hour per day for seven consecutive days, a nighttime heart rate threshold of approximately 85 beats per minute for seven consecutive days, a heart rate variability threshold of approximately 40 milliseconds for seven consecutive days, a cardiac resynchronization therapy percentage threshold of 90 percent for five of seven consecutive days, or an electrical shock threshold of 1 electrical shock. In other examples, each of the metric-specific thresholds may have various different values determined by the clinician, based on previous data from other patients, or determined based on a healthy state of patient 14. Alternatively, the metric-specific thresholds may be rate of change thresholds or relative change thresholds, e.g., a heart rate variability that is decreasing faster than a predetermined rate, or a predetermined amount or percentage less than a recently identified variability value.

In other examples, the heart failure risk level may be determined with probability models that determine the probability of hospitalization based on the values of all patient metrics. In this manner, each of the patient metric values may contribute to the risk level regardless of whether a metric-specific threshold is exceeded. For example, IMD 16 may generate a heart failure risk level with a Bayesian Belief Network based on the plurality of automatically generated patient metrics. The risk level may include general levels, e.g., a high risk, medium risk, or low risk of hospitalization, or numerical indications, e.g., a percent probability that patient 14 will be hospitalized. This risk level may be part of the lower resolution diagnostic information transmitted by IMD 16.

In addition to transmitting diagnostic information during a hospitalization period and a post-hospitalization period, IMD 16 may transmit lower resolution diagnostic information to a clinician or other user prior to the hospitalization period. In other words, IMD 16 may transmit a heart failure risk level to a clinician before patient 14 is ever admitted to the hospital for a heart failure decompensation event. The risk level transmitted may be similar to the post-hospitalization risk level, but, in some examples, the risk level transmitted prior to hospitalization may be transmitted less frequently, in response to an interrogation request from the clinician or other user, or upon the risk level reaching a more severe level, e.g., a high or medium risk of hospitalization.

During the post-hospitalization period, or during another period in which IMD 16 transmits lower resolution diagnostic information, IMD 16 may switch to transmitting higher resolution diagnostic information to the clinician once an elevated heart failure risk is detected. For example, if one or more of the automatically detected patient metrics exceeds its respective metric-specific threshold, IMD 16 may transmit that patient metric and possibly other patient metrics to allow the clinician to more accurately diagnose the problem with patient 14. This automatic switch from lower to higher resolution diagnostic information may enable the clinician to more quickly treat patient 14.

In addition, IMD 16 may alter the method with which patient metrics are stored within IMD 16. In other words, IMD 16 may store the automatically detected patient metrics with a dynamic data storage rate. The dynamic storage rate may be higher when IMD 16 is transmitting higher resolution diagnostic information and lower when IMD 16 is transmitting lower resolution diagnostic information. In addition to the dynamic storage rate, the rate at which IMD 16 automatically detects the patient metrics may be similarly altered to match the dynamic storage rate.

Before patient 14 is admitted to the hospital, e.g., before the hospitalization period, the clinician or admitting healthcare professional may submit an interrogation request to IMD 16 in order to retrieve a portion of the stored patient metrics. The patient metrics may help the clinician determine if hospitalization of patient 14 is a prudent action for treatment. In response to the interrogation request, IMD 16 may transmit at least some of the automatically detected patient metrics stored in IMD 16.

After patient 14 has been discharged from the hospital, or during the post-hospitalization period, the clinician may remotely interrogate IMD 16. This remote interrogation may initiate transmission of lower resolution diagnostic information from IMD 16 detected over a predetermined period of time. For example, IMD 16 may generate the heart failure risk level based on patient metrics detected over the previous seven day period of time. Since more recent patient metrics may be the most relevant, IMD 16 may use the predetermined period to limit the risk level to recent metrics. In other examples, IMD 16 may transmit lower resolution diagnostic information at predetermined intervals (e.g., once a day or once a week) or in response to a risk level change (e.g., generating a high risk level).

In other examples, a clinician or other healthcare professional at a clinic or hospital may remotely interrogate a plurality of IMDs of each of a plurality of patients. In other words, each IMD may be implanted in a different patient. In response to the remote interrogation request, each IMD may transmit lower resolution diagnostic information. A remote computing device may then receive the lower resolution diagnostic information and present the transmitted lower resolution diagnostic information to the user. The presented information may be arranged according to a hospitalization risk of each of the patients, e.g., a ranked listing of the patients according to hospitalization risk. This arrangement of patients may aid the clinician in triage of the patients or treating those patients requiring immediate medical attention.

Although the risk of heart failure may generally increase with increased fluid retention, these same patient metrics may also be used to determine when a patient is at a higher risk of dehydration in other examples. In this manner, the higher and lower resolution diagnostic information using patient metrics may be implemented to monitor a risk level for other disease states, e.g., renal dysfunction, dehydration, chronic obstructive pulmonary disease (COPD), and anemia.

Figure 2A:
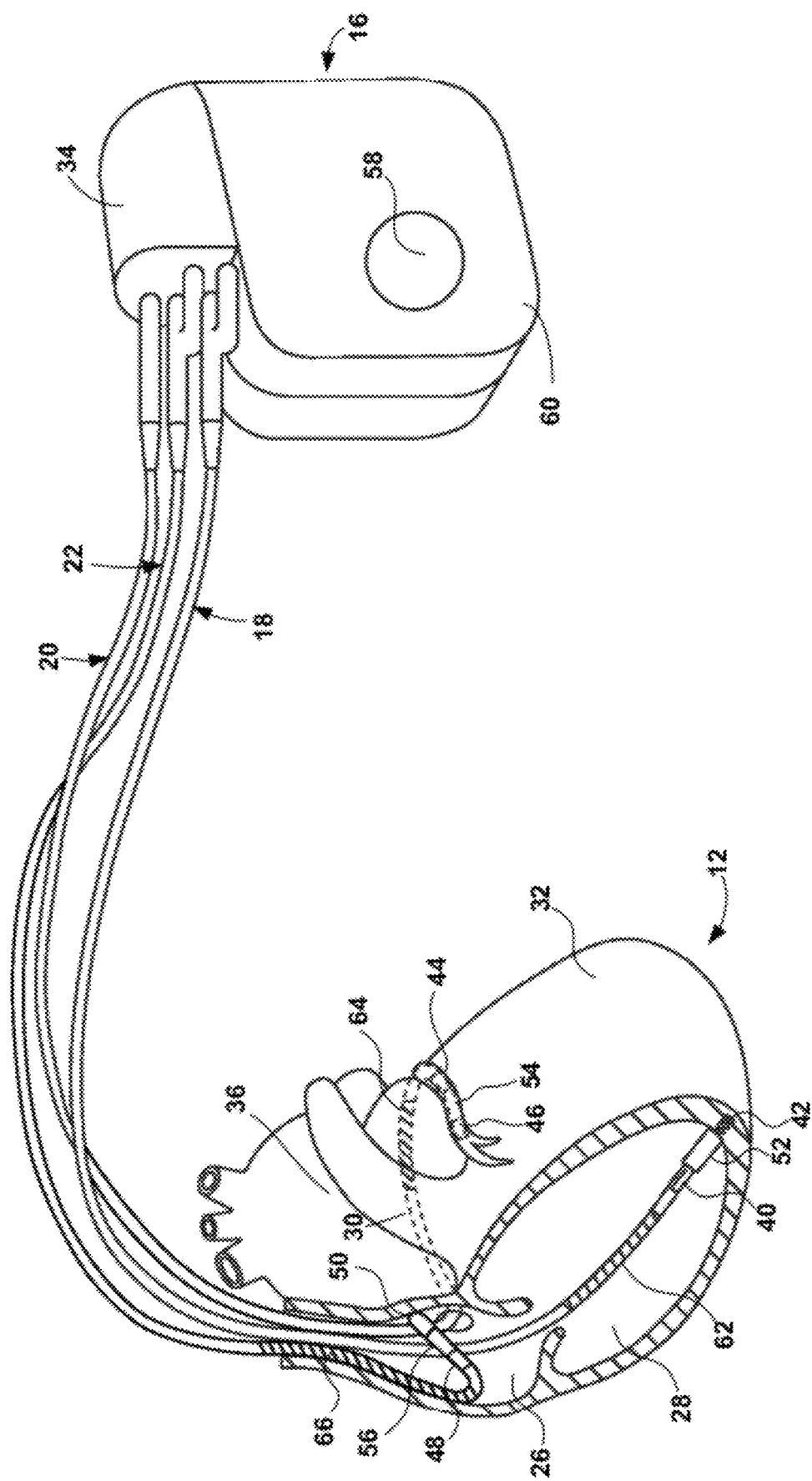
FIG. 2A is a conceptual drawing illustrating the example IMD and leads of FIG. 1 in conjunction with a heart.

FIG. 2A is a conceptual drawing illustrating IMD 16 and leads 18, 20, and 22 of system 10 in greater detail. As shown in FIG. 2A, IMD 16 is coupled to leads 18, 20, and 22. Leads 18, 20, 22 may be electrically coupled to a signal generator, e.g., stimulation generator, and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44, and 48 may take the form of ring electrodes, and electrodes 42, 46 and 50 may take the form of extendable helix tip electrodes mounted retractably within insulative electrode heads 52, 54 and 56, respectively. In other examples, one or more of electrodes 42, 46 and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

In some examples, as illustrated in FIG. 2A, IMD 16 includes one or more housing electrodes, such as housing electrode 58, which may be formed integrally with an outer surface of hermetically-sealed housing 60 of IMD 16, or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 3, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58. The combination of electrodes used for sensing may be referred to as a sensing configuration or electrode vector.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes. The combination of electrodes used for delivery of stimulation or sensing, their associated conductors and connectors, and any tissue or fluid between the electrodes, may define an electrical path.

The configuration of system 10 illustrated in FIGS. 1 and 2A is merely one example. In other examples, a system may include epicardial leads and/or subcutaneous electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may sense electrical signals and/or deliver defibrillation pulses and other therapies to heart 12 via percutaneous leads that extend through the skin of patient 14 to a variety of positions within or outside of heart 12. Further, external electrodes or other sensors may be used by IMD 16 to deliver therapy to patient 14 and/or sense and detect patient metrics used to generate the high and lower resolution diagnostic information, e.g., a heart failure risk level.

Figure 2B:
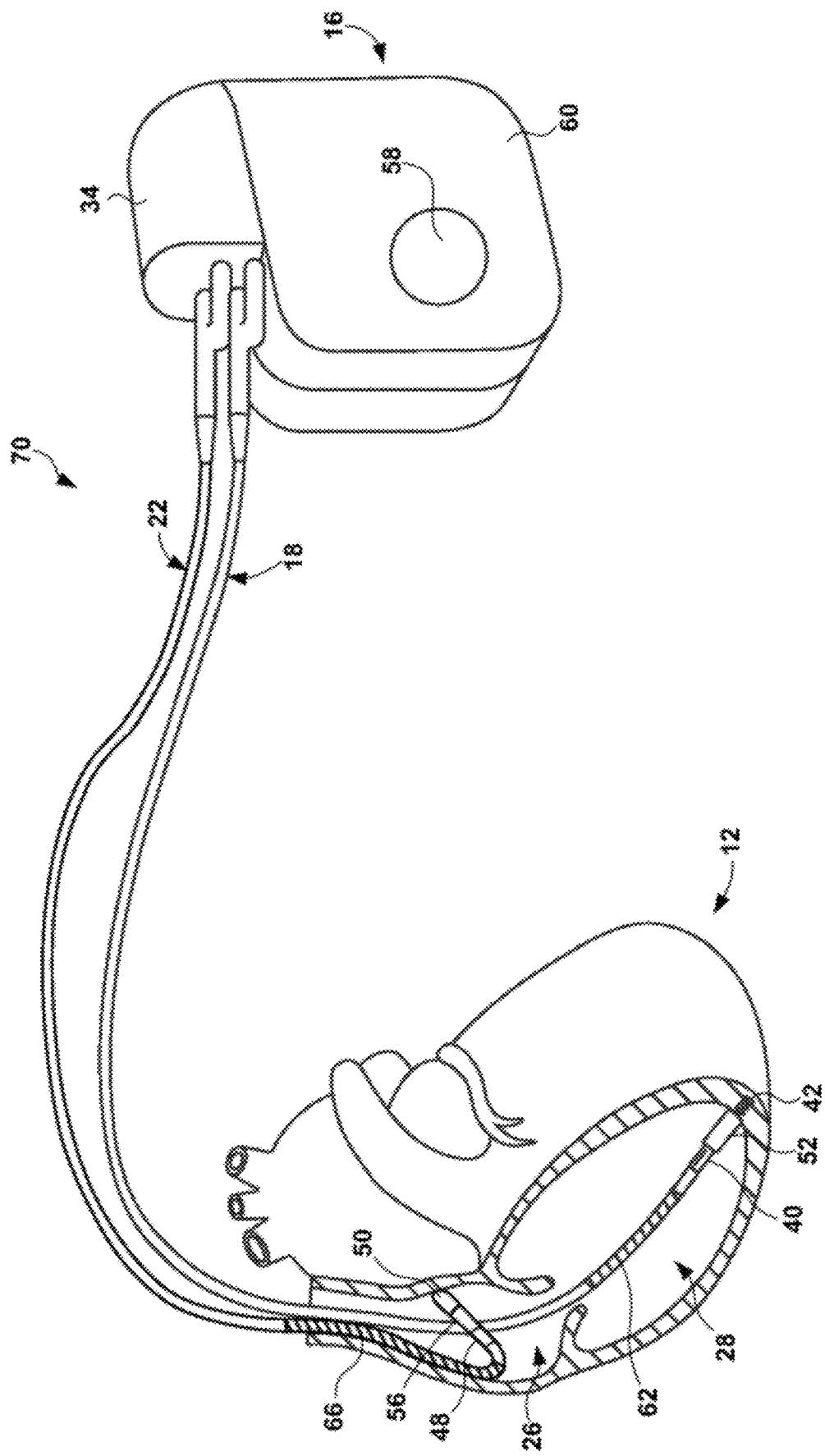
FIG. 2B is a conceptual drawing illustrating the example IMD of FIG. 1 coupled to a different configuration of implantable medical leads in conjunction with a heart.

In addition, in other examples, a system may include any suitable number of leads coupled to IMD 16, and each of the leads may extend to any location within or proximate to heart 12. For example, systems in accordance with this disclosure may include three transvenous leads located as illustrated in FIGS. 1 and 2, and an additional lead located within or proximate to left atrium 36. As another example, systems may include a single lead that extends from IMD 16 into right atrium 26 or right ventricle 28, or two leads that extend into a respective one of the right ventricle 26 and right atrium 26. An example of a two lead type of system is shown in FIG. 2B. Any electrodes located on these additional leads may be used in sensing and/or stimulation configurations.

Any of electrodes 40, 42, 44, 46, 48, 50, 62, 64, 66, and 58 may be utilized by IMD 16 to sense or detect patient metrics used to generate the heart failure risk level for patient 14. Typically, IMD 16 may detect and collect patient metrics from those electrode vectors used to treat patient 14. For example, IMD 16 may derive an atrial fibrillation duration, heart rate, and heart rate variability metrics from electrograms generated to deliver pacing therapy. However, IMD 16 may utilize other electrodes to detect these types of metrics from patient 14 when other electrical signals may be more appropriate for therapy.

In addition to electrograms of cardiac signals, any of electrodes 40, 42, 44, 46, 48, 50, 62, 64, 66, and 58 may be used to sense non-cardiac signals. For example, two or more electrodes may be used to measure an impedance within the thoracic cavity of patient 14. This intrathoracic impedance may be used to generate a fluid index patient metric that indicates the amount of fluid building up within patient 14. Since a greater amount of fluid may indicate increased pumping loads on heart 12, the fluid index may be used as an indicator of heart failure risk. IMD 16 may periodically measure the intrathoracic impedance to identify a trend in the fluid index over days, weeks, months, and even years of patient monitoring. During a hospitalization period, for example, the higher resolution diagnostic information transmitted by IMD 16 may include either the fluid index, intrathoracic impedance values, or other raw data usable by the clinician for monitoring fluid retention in patient 14.

In general, the two electrodes used to measure the intrathoracic impedance may be located at two different positions within the chest of patient 14. For example, coil electrode 62 and housing electrode 58 may be used as the sensing vector for intrathoracic impedance because electrode 62 is located within RV 28 and housing electrode 58 is located at the IMD 16 implant site generally in the upper chest region. However, other electrodes spanning multiple organs or tissues of patient 14 may also be used, e.g., an additional implanted electrode used only for measuring thoracic impedance.

FIG. 2B is a conceptual diagram illustrating another example system 70, which is similar to system 10 of FIGS. 1 and 2, but includes two leads 18, 22, rather than three leads. Leads 18, 22 are implanted within right ventricle 28 and right atrium 26, respectively. System 70 shown in FIG.

2B may be useful for physiological sensing and/or providing pacing, cardioversion, or other therapies to heart 12. Detection of patient metrics and transmission of high and lower resolution diagnostic information according to this disclosure may be performed in two lead systems in the manner described herein with respect to three lead systems. In other examples, a system similar to systems 10 and 70 may only include one lead (e.g., any of leads 18, 20 or 22) to deliver therapy and/or sensor and detect patient metrics related to monitoring risk of heart failure. Alternatively, the lower and higher resolution diagnostic information may be implemented in systems utilizing subcutaneous leads, subcutaneous IMDs, or even external medical devices.

Figure 3:
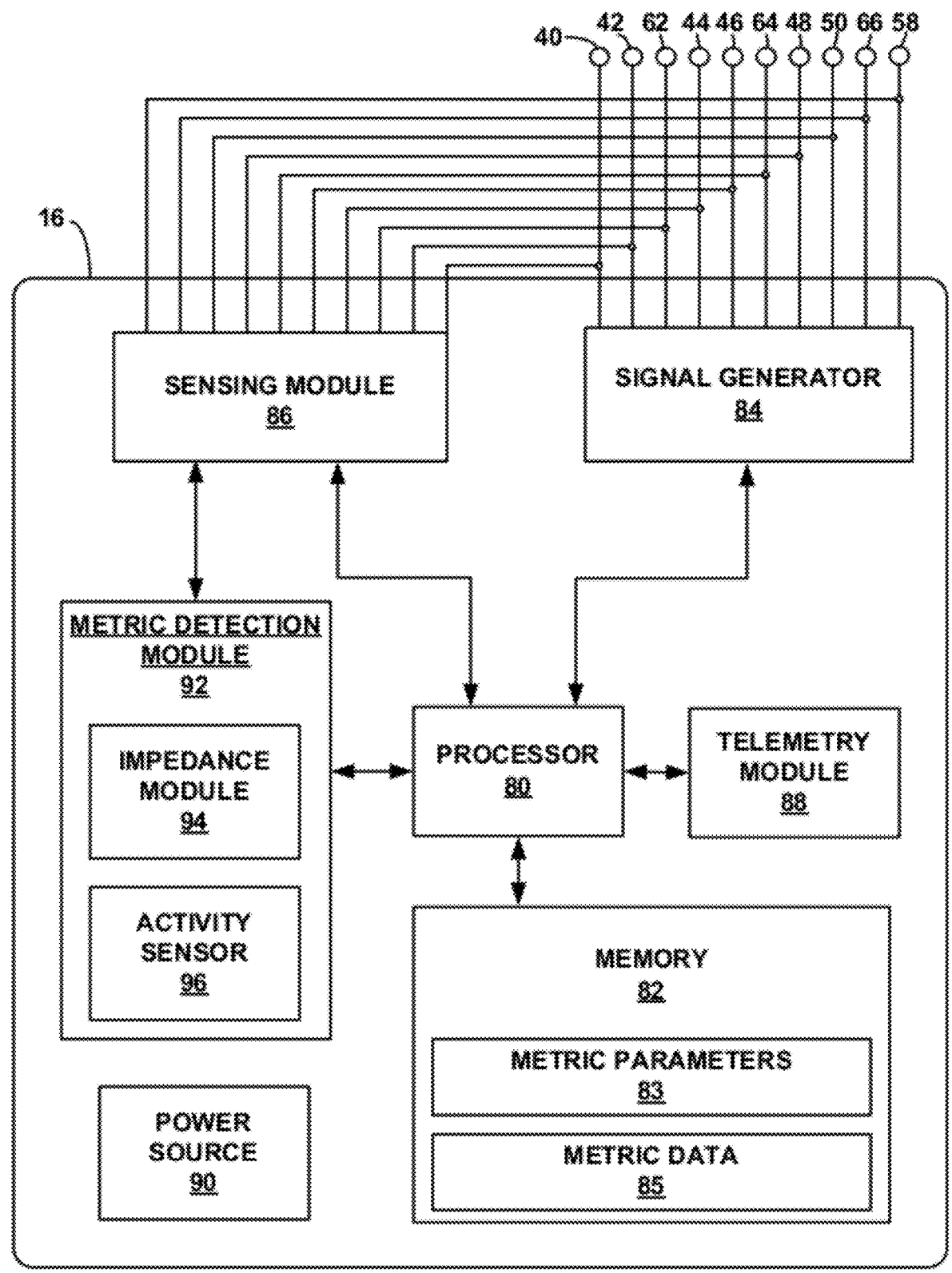
FIG. 3 is a functional block diagram illustrating an example configuration of the IMD of FIG. 1.

FIG. 3 is a functional block diagram illustrating an example configuration of IMD 16. In the illustrated example, IMD 16 includes a processor 80, memory 82, metric detection module 92, signal generator 84, sensing module 86, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver stimulation therapy to heart 12 according to a therapy parameters, which may be stored in memory 82. For example, processor 80 may control signal generator 84 to deliver electrical pulses with the amplitudes, pulse widths, frequency, or electrode polarities specified by the therapy parameters.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. In the illustrated example, signal generator 84 is configured to generate and deliver electrical stimulation therapy to heart 12. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator may deliver one or more of these types of stimulation in the form of other signals, such as sine waves, square waves, or other substantially continuous time signals.

Signal generator 84 may include a switch module and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Electrical sensing module 86 monitors signals from at least one of electrodes 40, 42, 44, 46, 48, 50, 58, 62, 64 or 66 in order to monitor electrical activity of heart 12, impedance, or other electrical phenomenon. Sensing may be done to determine heart rates or heart rate variability, or to detect arrhythmias or other electrical signals. Sensing module 86 may also include a switch module to select which of the available electrodes are used to sense the heart activity, depending upon which electrode combination, or electrode vector, is used in the current sensing configuration. In some examples, processor 80 may select the electrodes that function as sense electrodes, i.e., select the sensing configuration, via the switch module within sensing module 86. Sensing module 86 may include one or more detection channels, each of which may be coupled to a selected electrode configuration for detection of cardiac signals via that electrode configuration. Some detection channels may be configured to detect cardiac events, such as P- or R-waves, and provide indications of the occurrences of such events to processor 80, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processor 80 may control the functionality of sensing module 86 by providing signals via a data/address bus.

Processor 80 may include a timing and control module, which may be embodied as hardware, firmware, software, or any combination thereof. The timing and control module may comprise a dedicated hardware circuit, such as an ASIC, separate from other processor 80 components, such as a microprocessor, or a software module executed by a component of processor 80, which may be a microprocessor or ASIC. The timing and control module may implement programmable counters. If IMD 16 is configured to generate and deliver pacing pulses to heart 12, such counters may control the basic time intervals associated with DDD, VVI, DVI, VDD, AAI, DDI, DDDR, VVIR, DVIR, VDDR, AAIR, DDIR, CRT, and other modes of pacing.

Intervals defined by the timing and control module within processor 80 may include atrial and ventricular pacing escape intervals, refractory periods during which sensed P-waves and R-waves are ineffective to restart timing of the escape intervals, and the pulse widths of the pacing pulses. As another example, the timing and control module may withhold sensing from one or more channels of sensing module 86 for a time interval during and after delivery of electrical stimulation to heart 12. The durations of these intervals may be determined by processor 80 in response to stored data in memory 82. The timing and control module of processor 80 may also determine the amplitude of the cardiac pacing pulses.

Interval counters implemented by the timing and control module of processor 80 may be reset upon sensing of R-waves and P-waves with detection channels of sensing module 86. In examples in which IMD 16 provides pacing, signal generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. In such examples, processor 80 may reset the interval counters upon the generation of pacing pulses by signal generator 84, and thereby control the basic timing of cardiac pacing functions, including anti-tachyarrhythmia pacing.

The value of the count present in the interval counters when reset by sensed R-waves and P-waves may be used by processor 80 to measure the durations of R-R intervals, P-P intervals, P-R intervals and R-P intervals, which are measurements that may be stored in memory 82. Processor 80 may use the count in the interval counters to detect a tachyarrhythmia event, such as atrial fibrillation (AF), atrial tachycardia (AT), ventricular fibrillation (VF), or ventricular tachycardia (VT). These intervals may also be used to detect the overall heart rate, ventricular contraction rate, and heart rate variability. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies may also be employed by processor 80 in other examples.

In some examples, processor 80 may determine that tachyarrhythmia has occurred by identification of shortened R-R (or P-P) interval lengths. Generally, processor 80 detects tachycardia when the interval length falls below 220 milliseconds (ms) and fibrillation when the interval length falls below 180 ms. These interval lengths are merely examples, and a user may define the interval lengths as desired, which may then be stored within memory 82. This interval length may need to be detected for a certain number of consecutive cycles, for a certain percentage of cycles within a running window, or a running average for a certain number of cardiac cycles, as examples.

In the event that processor 80 detects an atrial or ventricular tachyarrhythmia based on signals from sensing module 86, and an anti-tachyarrhythmia pacing regimen is desired, timing intervals for controlling the generation of anti-tachyarrhythmia pacing therapies by signal generator 84 may be loaded by processor 80 into the timing and control module to control the operation of the escape interval counters therein and to define refractory periods during which detection of R-waves and P-waves is ineffective to restart the escape interval counters for the an anti-tachyarrhythmia pacing. In the event that processor 80 detects an atrial or ventricular tachyarrhythmia based on signals from sensing module 86, and a cardioversion or defibrillation shock is desired, processor 80 may control the amplitude, form and timing of the shock delivered by signal generator 84.

Memory 82 may be configured to store a variety of operational parameters, therapy parameters, sensed and detected data, and any other information related to the therapy and treatment of patient 14. In the example of FIG. 3, memory 82 also includes metric parameters 83 and metric data 85. Metric parameters 83 may include all of the parameters and instructions required by processor 80 and metric detection module 92 to sense and detect each of the patient metrics used to generate the high and lower resolution diagnostic information transmitted by IMD 16. Metric data 85 may store all of the data generated from the sensing and detecting of each patient metric. In this manner, memory 82 stores a plurality of automatically detected patient metrics as the data required to generate a risk level of patient 14 being admitted to the hospital due to heart failure.

Metric parameters 83 may include definitions of each of the patient metrics automatically sensed or measured by metric detection module 92. These definitions may include instructions regarding what electrodes or sensors to use in the detection of each metric, the sample rate, calibration schemes, metric-specific thresholds, and any other related information. In one example, the patient metrics for which metric parameters are stored as metric parameters 83 may include a thoracic fluid index (or a thoracic impedance), an atrial tachycardia or fibrillation burden, a ventricular contraction rate during atrial fibrillation, a patient activity, a nighttime heart rate, a difference between night and day heart rate, a heart rate variability, a cardiac resynchronization therapy percentage, a bradyarrhythmia pacing therapy percentage (in a ventricle and/or atrium), and number or frequency of electrical shock events. In other examples, other patient metrics may be stored that may be useful in the detection of heart failure risk, e.g., blood pressure, right ventricular pressure, pulmonary artery pressure, patient temperature, lung volume, lung tidal volume, lung density, breathing rate or even biomarkers such as a brain natriuretic peptide (BNP), troponin, or related surrogates. In such examples, IMD 16 may include or be coupled to sensors known in the art for detecting such metrics. In some examples, the atrial tachycardia or fibrillation burden may be a time of the event, a percent or amount of time over a certain period, a number of episodes, or even a frequency of episodes. IMD 16 may transmit one or more of these patient metrics to a user as the higher resolution diagnostic information.

Generally, the higher resolution diagnostic information may include metrics detected at a greater frequency and/or metrics with greater detail than the lower resolution diagnostic information. For example, the higher resolution diagnostic information may include values of the at least one patient metric, or other raw data, detected at least once every two hours or on-demand during the hospitalization period, for example. In other examples, the higher resolution diagnostic information may include metrics detected at other frequencies, e.g., once every four hours, once every hour, or once every ten minutes. In addition, or alternatively, the higher resolution diagnostic information may include information for more specific data, e.g., specific patient metric values, raw data, or other detailed information. During the hospitalization period, processor 80 may transmit the higher resolution diagnostic information via telemetry module 88 to be presented to and interpreted by a clinician to treat patient 14. In some examples, the higher resolution diagnostic information may used by the clinician to determine when to discharge patient 14 from the hospital, i.e., end the hospitalization period. For example, the clinician may use the thoracic impedance value from the higher resolution diagnostic information to identify when diuretics given to patient 14 have reduced fluid retention to a less critical value.

In addition to, or as an alternative to using the higher resolution diagnostic information to determine whether to discharge a patient, the collection and transmission of higher resolution diagnostic information may be triggered based on an elevated lower resolution diagnostic information risk level. The clinician may review the higher resolution diagnostic information to determine if patient 14 needs to be evaluated in a clinical setting or even admitted to a hospital for worsening heart failure. In this manner, review of higher resolution diagnostic information may not be limited to a hospitalization period of patient 14.

Metric parameters 83 may also store a metric-specific threshold for each of the patient metrics automatically detected by metric detection module 92. Metric thresholds may be predetermined and held constant over the entire monitoring of patient 14. In some examples, however, metric thresholds may be modified by a user during therapy or processor 80 may automatically modify one or more metric thresholds to compensate for certain patient conditions. For example, a heart rate threshold may be changed over the course of monitoring if the normal or baseline heart rate has changed during therapy.

In one example, these metric-specific thresholds may include a thoracic fluid index threshold of approximately 60, an atrial fibrillation burden threshold of approximately 6 consecutive hours, a ventricular contraction rate threshold approximately equal to 90 beats per minute for 24 hours, a patient activity threshold approximately equal to 1 hour per day for seven consecutive days, a nighttime heart rate threshold of approximately 85 beats per minute for seven consecutive days, a heart rate variability threshold of approximately 40 milliseconds for seven consecutive days, a cardiac resynchronization therapy percentage threshold of 90 percent for five of seven consecutive days, and an electrical shock number threshold of 1 electrical shock. These thresholds may be different in other examples, and may be configured by a user, e.g., a clinician, for an individual patient.

Processor 80 may alter the method with which patient metrics are stored in memory 82 as metric data 85. In other words, processor 80 may store the automatically detected patient metrics with a dynamic data storage rate. The dynamic storage rate may be higher when processor 80 needs to transmit higher resolution diagnostic information and lower when processor 80 needs to transmit lower resolution diagnostic information. For example, processor 80 may store patient metrics in memory 82 every minute or hour when processor 80 is transmitting higher resolution diagnostic information. However, processor 80 may only store patient metrics in memory 82 once a day, for example, when processor 80 is only transmitting lower resolution diagnostic information that does not necessitate more frequent data. In addition to the dynamic storage rate, the rate at which metric detection module 92 automatically detects each patient metric may be altered to match the dynamic storage rate. In this manner, metric detection module 92 may not waste energy detecting patient metrics if the higher frequency data would just be discarded.

Metric detection module 92 may, for example, transmit lower resolution diagnostic information (e.g., a heart failure risk level) that is based on the patient metrics and whether any of the metrics exceed the respective specific metric thresholds. Any time that an automatically detected patient metric exceeds their respective metric threshold, the patient metric is counted in the risk level. In one example, if two or more of the eight patient metrics exceed their respective metric threshold, then the risk level would be classified as a high risk. In other examples, the risk level may include a numerical value such as 2 out of 8 (e.g., threshold exceeding metrics out of the total number of monitored metrics). The higher the risk level, the more likely that patient 14 is at risk to be admitted to the hospital within a predefined time period, e.g., re-admitted to the hospital within a post-hospitalization period. For example, each threshold exceeding metric counted in the predetermined number may contribute to a higher risk level of heart failure. In this example, a risk level of 1 out of 8 may indicate a medium risk of hospitalization, a risk level of 2 out of 8 may indicate a high level of hospitalization, and a risk level of 3 out of 8 may indicate a very high risk of hospitalization.

It is also noted that exceeding a metric threshold does not require that the detected value of the patient metric becomes greater than the magnitude of the threshold. For some patient metrics, exceeding the metric threshold may occur when the value of the patient metric drops below the metric threshold. Therefore, each threshold may be a boundary that triggers the metric's inclusion in the heart failure risk level any time that the metric threshold is crossed. In other examples, as described above, the risk level may be calculated as a sum of weighted metrics such that some metrics may impact the risk level greater than other metrics (e.g., a trans-thoracic impedance may be weighted double that of other metrics). This use of thresholds for determining the risk levels may be considered heuristic logic.

In this manner, metric detection module 92 may automatically detect each of the patient metrics and store them within metric data 85 for later transmission. During a hospitalization period of patient 14, telemetry module 88 may transmit higher resolution diagnostic information to a user, e.g., a clinician or other health care professional. The higher resolution diagnostic information may be based on at least one of the plurality of patient metrics, and the higher resolution diagnostic information may also be indicative of heart failure. During a post-hospitalization period of patient 14, telemetry module 88 may transmit lower resolution diagnostic information to the user. The lower resolution diagnostic information may be generated by metric detection module 92 and based on the plurality of patient metrics and be indicative of a potential hospitalization period due to heart failure. Metric detection module 92 may be any type of hardware (e.g., a specialized circuit or processor) or a software module executed by a processor (e.g., processor 80).

Metric parameters 83 may generally store one metric-specific threshold per patient metric, but other examples may include several thresholds to apply depending on other patient conditions, delivered therapies, or even the importance of one patient metric. For example, the thoracic fluid index determined from sensed intrathoracic impedance may be subject to two separate metric thresholds each counting towards the predetermined number of the heart failure risk level. The first thoracic fluid index threshold may be set to a value of 60, but the second thoracic fluid index threshold may be set to a value of 100. If the thoracic fluid index metric exceeds the first thoracic fluid index threshold of 60, the fluid index metric may be counted in the heart failure risk level. If the fluid index also crosses the second thoracic fluid index threshold of 100, the fluid index metric may be counted in the heart failure risk level a second time. In this manner, the heart failure risk level may weight more extreme values of some metrics more heavily than other metrics. In one example, the fluid index value may be a unitless number using a recent intrathoracic impedance, a short term mean impedance, an impedance variability value, and a duration value. Example fluid index values and impedance measurements are described in U.S. Patent Application No. 2010/0030292 entitled "DETECTING WORSENING HEART FAILURE BASED ON IMPEDANCE MEASUREMENTS," which is incorporated by reference herein in its entirety. As the intrathoracic impedance remains low, the fluid index may increase. Conversely, as the intrathoracic impedance remains high, the fluid index may decrease. In this manner, the fluid index value maybe a numerical representation of retained fluid that is specific to patient 14. In other examples, the intrathoracic impedance may be alternatively used.

In other examples, a statistical or probability analysis may be performed on some or all of the patient metrics to determine the probability that patient 14 will be re-hospitalized for heart failure. In this manner, the heart failure risk level may be determined without utilizing thresholds for each of the detected patient metrics. Instead, metric detection module 92 or processor 80 may examine the values of each of the patient metrics for relative contributions to the possibility that patient 14 is at a higher risk of being re-hospitalized. For example, a Bayesian Belief Network may use the values of the patient metrics instead of a predetermined threshold to determine the risk level that patient 14 will be re-admitted to the hospital for heart failure. Such a statistical analysis is described in PCT Patent Publication No. WO 2011/126823A1 entitled, "METHOD AND APPARATUS FOR MONITORING TISSUE FLUID CONTENT FOR USE IN AN IMPLANTABLE CARDIAC DEVICE," which is incorporated by reference herein in its entirety.

In either case, metric data 85 may be used as a basis for processor 80 to generate lower resolution diagnostic information. Patient metrics used for lower resolution diagnostic information may include patient metric values detected with lesser frequency than the higher resolution diagnostic information and/or generalized information instead of specific patient metric values. For example, the lower resolution diagnostic information may include the heart failure risk level that indicates the likelihood that patient 14 will be admitted to the hospital due to heart failure within a predetermined period. The likelihood may be a risk that patient 14 will be re-hospitalized within a predetermined time period, e.g., 30 days. In one example, the risk level may be generalized into different categories, e.g., high risk, medium risk, and low risk. These categories of the risk level may be determined using metric-specific thresholds, a statistical analysis of the patient metrics, or other such analysis technique. In other examples, the risk level may be numerical to more precisely define the risk of patient 14. A clinician may select how the lower resolution diagnostic information may be delivered.

Metric parameters 83 may also store instructions for generating the heart failure risk level and thresholds for when the risk level is transmitted, or pushed, to a clinician. For example, a generated high risk level may cause IMD 16 to transmit the lower resolution diagnostic information without an interrogation request. Although the heart failure risk level may be delivered and presented to users at any time, the heart failure risk level may be pushed to a user when it indicates an increased risk of heart failure. The risk level may become critical when the predetermined number of patient metrics, for example, each exceed their respective metric-specific threshold. For example, if the predetermined number is set at two to indicate a high risk, then the heart failure risk level becomes critical when two patient metrics each exceed their respective threshold. Once the heart failure risk level is critical, processor 80 may push the risk level to a user at a remote location since patient 14 requires medical treatment to avoid heart failure, reduce any damage caused by the condition, and prevent hospitalization of patient 14.

Metric data 85 is a portion of memory 82 that may store some or all of the patient metric data that is sensed and detected by metric detection module 92. Metric data 85 may store the data for each metric on a rolling basis during an evaluation window. The evaluation window may only retain recent data and delete older data from the evaluation window when new data enters the evaluation window. In this manner, the evaluation window may include only recent data for a predetermined period of time. Processor 80 may access metric data when necessary to retrieve and transmit patient metric data and/or generate heart failure risk levels. In addition, metric data 85 may store heart failure risk levels or other generated information related to the heart failure risk of patient 14. The data stored in metric data 85 may be transmitted as part of higher resolution diagnostic information or lower resolution diagnostic information. Although metric parameters 83 and/or metric data 85 may consist of separate physical memories, these components may simply be an allocated portion of the greater memory 82.

Metric detection module 92 may automatically sense and detect each of the patient metrics. Metric detection module 92 may then generate lower resolution diagnostic information, e.g., risk levels, based on the patient metrics. For example, metric detection module 92 may measure the thoracic impedance, analyze an electrogram of heart 12, monitor the electrical stimulation therapy delivered to patient 14, or sense the patient activity. It is noted that functions attributed to metric detection module 92 herein may be embodied as software, firmware, hardware or any combination thereof. In some examples, metric detection module 92 may at least partially be a software process executed by processor 80. Metric detection module 92 may sense or detect any of the patient metrics used as a basis for generating the heart failure risk level or otherwise indication of heart failure status or that patient 14 is at risk for hospitalization. In one example, metric detection module 92 may compare each of the patient metrics to their respective metric-specific thresholds defined in metric parameters 83 to generate the heart failure risk level. Metric detection module 92 may automatically detect two or more patient metrics. In other examples, metric detection module 92 may detect eight different patient metrics.

In one example, metric detection module 92 may analyze electrograms received from sensing module 86 to detect an atrial fibrillation or atrial tachycardia, and determine atrial tachycardia or fibrillation burden, e.g., duration, as well as a ventricular contraction rate during atrial fibrillation. Metric detection module 92 may also analyze electrograms in conjunction with a real-time clock, patient posture or activity signal, e.g., from activity sensor 96, and/or other physiological signals indicative of when a patient is asleep or awake to determine a nighttime (or sleeping) heart rate or a daytime (or awake) heart rate or a difference between the day and night heart rate, and also analyze electrograms to determine a heart rate variability, or any other detectable cardiac events from one or more electrograms. As described above, metric detection module 92 may use peak detection, interval detection, or other methods to analyze the electrograms.

In addition, metric detection module 92 may include and/or control impedance module 94 and activity sensor 96. Impedance module 94 may be used to detect the thoracic impedance used to generate the thoracic fluid index. As described herein, impedance module 94 may utilize any of the electrodes of FIG. 1, 2 or 3 to take intrathoracic impedance measurements. In other examples, impedance module 94 may utilize separate electrodes coupled to IMD 16 or in wireless communication with telemetry module 88. Once impedance module 94 measures the intrathoracic impedance of patient 14, metric detection module 92 may generate the thoracic fluid index and compare the index to the thoracic fluid index threshold defined in metric parameters 83.

Activity sensor 96 may include one or more accelerometers or other devices capable of detecting motion and/or position of patient 14. Activity sensor 96 may therefore detect activities of patient 14 or postures engaged by patient 14. Metric detection module 92 may, for example, monitor the patient activity metric based on the magnitude or duration of each activity and compare the determined metric data to the activity threshold defined in metric parameters 83. The activity patient metric may then be used to generate the heart failure risk level.

In addition to detecting events of patient 14, metric detection module 92 may also detect certain therapies delivered by signal generator 84, e.g., as directed by processor 80. Metric detection module 92 may monitor signals through signal generator 84 or receive therapy information directly from processor 80 for the detection. Example patient metrics detected by this method may include a cardiac resynchronization therapy percentage or metrics related to delivery of electrical shocks.

The cardiac resynchronization therapy (CRT) metric may be the amount or percentage of time each day, or an amount of percentage of cardiac cycles, as examples, that IMD 16 delivers cardiac resynchronization therapy to heart 12. Low CRT amounts or percentages may indicate that beneficial therapy is not being delivered and that adjustment of therapy parameters, e.g., an atrioventricular delay or a lower pacing rate, may improve therapy efficacy. In one example, higher CRT amounts or percentages may indicate that heart 12 is sufficiently pumping blood through the vasculature with the aid of therapy to prevent fluid buildup. In examples of other types of cardiac pacing (non-CRT) or stimulation therapy, higher therapy percentages may indicate that heart 12 is unable to keep up with blood flow requirements.

An electrical shock may be a defibrillation event or other high energy shock used to return heart 12 to a normal rhythm. The metric related electrical shocks may be a number or frequency of electrical shocks, e.g., a number of shocks within a period of time. Metric detection module 92 may detect these patient metrics as well and compare them to a cardiac resynchronization therapy percentage and shock event threshold, respectively, defined in metric parameters 83 to determine when each patient metric has become critical. In one example, the electrical shock event metric may become critical when a threshold number of shocks is delivered, e.g., within a time period, or even when patient 14 even receives one therapeutic shock.

Metric detection module 92 may include additional submodules or sub-routines that detect and monitor other patient metrics used to monitor patient 14 and/or generate the heart failure risk level. In other words, metric detection module 92 may include additional components to generate both the higher and lower resolution diagnostic information. In some examples, metric detection module 92, or portions thereof, may be incorporated into processor 80 or sensing module 86. In other examples, raw data used to produce patient metric data may be stored in metric data 85 for later processing or transmission to an external device. An external device may then produce each patient metric from the raw data, e.g., electrogram or intrathoracic impedance. In other examples, metric detection module 92 may additionally receive data from one or more implanted or external devices used to detect each metric which IMD 16 may store as metric data.

In some examples, the patient metric thresholds used to generate the risk levels may change over time, e.g., the patient metric thresholds may either be modified by a user or automatically changed based on other patient conditions. Telemetry module 88 may receive commands from programmer 24, for example, to modify one or more metric parameters 83 (e.g., metric creation instructions or metric-specific thresholds). In some examples, processor 80 may automatically adjust a metric-specific threshold if certain conditions are present in patient 14. For example, the threshold may be adjusted if patient 14 is experiencing certain arrhythmias or data contained in cardiac electrograms change, e.g., there is a deviation in ST elevations or presence of pre-ventricular contractions, in such a manner that requires a change in the threshold.

Processor 80 may generate the heart failure risk level based upon the patient metrics sensed, detected, and stored in metric data 85 of memory 82. For example, processor 80 may continually update the heart failure risk level as metric detection module 92 updates each patient metric. In other examples, processor 80 may periodically update the heart failure risk level according to an updating schedule. For example, processor 80 may generate the risk level once a day, e.g., during the post-hospitalization period, for transmission as lower resolution diagnostic information. Processor 80 may compare each of the automatically detected patient metrics to their respective metric-specific thresholds and automatically generate the heart failure risk level based on the comparison.

Processor 80 may also compare the heart failure risk level to the predetermined number stored in memory 82. The predetermined number may indicate when patient 14 is at an increased risk of heart failure. The predetermined number may be a percentage or a number of patient metrics exceeding the respective metric threshold. At this stage, the risk level may be considered critical. Although a clinician may be presented with the heart failure risk level at any time, processor 80 may push the heart failure risk level to a clinician or other healthcare professional in an alert. This immediacy may be necessary because a critical risk level indicates that heart failure may be imminent in a large number of patients with the same patient metric levels. Therefore, a clinician may receive the transmitted lower resolution diagnostic information of the critical risk level and initiate alternative treatment to prevent patient 14 from hospitalization.

In some examples, programmer 24, a computing device, or a server may thus include a metric detection module similar to metric detection module 92 described herein. For example, programmer 24 may generate the risk level based on higher resolution diagnostic information, including patient metric values, transmitted by IMD 16. However, processor 80 may still collect and store the data for each patient metric or even organize and format the patient metric data before transmitting the patient metrics in metric data 85 to the external device. In addition, processor 80 may transmit the metric thresholds with the patient metric data so that any external device may generate heart failure risk levels specific to patient 14.

As described above, processor 80 may provide an alert to a user, e.g., of programmer 24, regarding the data from any patient metric and/or the heart failure risk level. In one example, processor 80 may provide an alert with the heart failure risk level when programmer 24 or another device communicates with IMD 16. This communication may be in the form of an interrogation request that is sent to IMD 16. In response to the interrogation request, processor 80 may transmit higher resolution diagnostic information if patient 14 is hospitalized or lower resolution diagnostic information if patient 14 is in the post-hospitalization period. In other examples, processor 80 may push an alert to programmer 24 or another device whenever the heart failure risk level becomes critical via transmission by telemetry module 88. Alternatively, IMD 16 may directly indicate to patient 14 that medical treatment is needed due to a critical heart failure risk level. IMD 16 may include a speaker to emit an audible sound through the skin of patient 14 or a vibration module that vibrates to notify patient 14 of needed medical attention. Processor 80 may choose this action, for example, if the alert cannot be sent because of no available connection.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data (higher or lower resolution diagnostic information) to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals, e.g., EGMs, produced by atrial and ventricular sense amplifier circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac events that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

In some examples, IMD 16 may signal programmer 24 to further communicate with and pass the alert through a network such as the Medtronic CareLink® Network developed by Medtronic, Inc., of Minneapolis, Minn., or some other network linking patient 14 to a clinician. In this manner, a computing device or user interface of the network may be the external computing device that delivers the alert, e.g., patient metric data in the form of higher resolution diagnostic information or heart failure risk level in the form of lower resolution diagnostic information, to the user. IMD 16 may spontaneously transmit the diagnostic information to the network or in response to an interrogation request from a user. In other examples, one or more steps in the generation of the heart failure risk level may occur within a device external of patient 14, e.g., within programmer 24 or a server networked to programmer 24. In this manner, IMD 16 may detect and store patient metrics before transmitting the patient metrics to a different computing device. Patient metrics may, in some examples, be compared to means, medians, or outliers from other patients to determine when the patient is at a high risk of hospitalization for heart failure.

In addition to transmitting diagnostic information during a hospitalization period and a post-hospitalization period, processor 80 may control telemetry module 88 to transmit lower resolution diagnostic information to a clinician or other user prior to the hospitalization period. In other words, IMD 16 may transmit a heart failure risk level to a clinician before patient 14 is admitted to the hospital for heart failure. This lower resolution diagnostic information may be a part of general monitoring tasks of IMD 16. The risk level transmitted may be similar to the post-hospitalization risk level, but, in some examples, the risk level transmitted prior to hospitalization may be transmitted less frequently, e.g., in response to an interrogation request from the clinician or other user, or upon the risk level reaching a severe level, e.g., a high or medium risk of hospitalization.

Before patient 14 is admitted to the hospital, e.g., before the hospitalization period, the clinician or admitting healthcare professional may submit an interrogation request to IMD 16 in order to retrieve a portion of the patient metrics stored as metric data 85. The previously stored patient metrics may help the clinician determine if hospitalization of patient 14 is a prudent action for treatment. In response to the interrogation request, processor 80 may control telemetry module 88 to transmit at least some of the automatically detected patient metrics stored in memory 82.

During the post-hospitalization period, or during another period in which IMD 16 transmits lower resolution diagnostic information, processor 80 may control telemetry module 88 to switch to transmitting higher resolution diagnostic information to the clinician once an elevated heart failure risk is detected (e.g., a medium risk or high risk of heart failure). For example, if one of the automatically detected patient metrics exceeds its respective metric-specific threshold, processor 80 may control telemetry module to transmit that patient metric and possibly other patient metrics to allow the clinician to more accurately diagnose the problem with patient 14. This automatic switch from lower to higher resolution diagnostic information may enable the clinician to more quickly treat patient 14.

After patient 14 has been discharged from the hospital, or during the post-hospitalization period, the clinician may remotely interrogate IMD 16 via telemetry module 88. This remote interrogation may initiate transmission of lower resolution diagnostic information from memory 82, or generation of the lower resolution diagnostic information based on metric data 85, detected over a predetermined period of time. For example, processor 80 may generate the heart failure risk level based on patient metrics detected over the predetermined period of time that is the previous seven days. Generally, the predetermined period of time may be between approximately one day and 30 days. However, the risk level may be generated based on periods of time greater than 30 days. Since more recent patient metrics may be the most relevant, IMD 16 may use the predetermined period to limit the risk level to recently detected metrics. In other examples, processor 80 may control telemetry module 88 to transmit lower resolution diagnostic information at predetermined intervals (e.g., once a day or once a week) or in response to a risk level change (e.g., generating a high risk level).

In some examples, IMD 16 may automatically provide therapy to patient 14 based on the heart failure risk level and/or one of the patient metrics. For example, IMD 16 or another device may include a drug pump that delivers a dose of medication, e.g., nitroglycerin, to alleviate the imminent or present heart failure conditions. This drug pump may be in addition to or in place of electrical stimulation therapy devices. In some examples, IMD 16 may deliver pacing therapy to try and reduce the heart failure symptoms.

Figure 4:
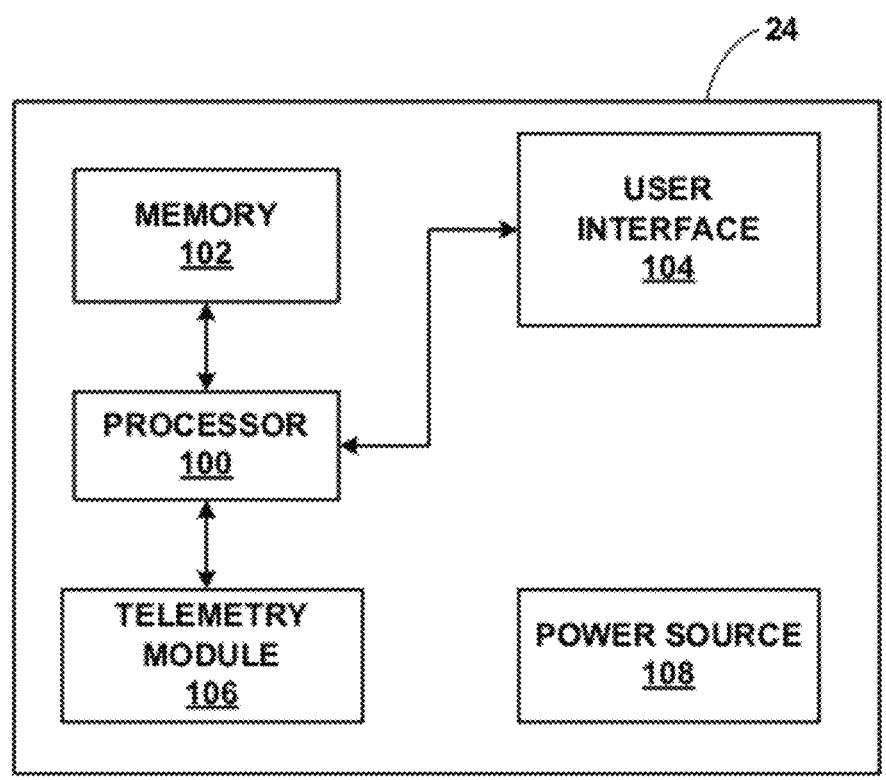
FIG. 4 is a functional block diagram illustrating an example configuration of an external programmer that facilitates user communication with the IMD.

FIG. 4 is a functional block diagram illustrating an example configuration of external programmer 24. As shown in FIG. 4, programmer 24 may include a processor 100, memory 102, user interface 104, telemetry module 106, and power source 108. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to configure the operational parameters of and retrieve data from IMD 16 (FIG. 1). The clinician may interact with programmer 24 via user interface 104, which may include display to present graphical user interface to a user, and a keypad or another mechanism for receiving input from a user. In addition, the user may receive an alert or notification from IMD 16 indicating the heart failure risk level and/or patient metrics via programmer 24. In other words, programmer 24 may receive higher or lower resolution diagnostic information from IMD 16.

Processor 100 can take the form one or more microprocessors, DSPs, ASICs, FPGAs, programmable logic circuitry, or the like, and the functions attributed to processor 100 herein may be embodied as hardware, firmware, software or any combination thereof. Memory 102 may store instructions that cause processor 100 to provide the functionality ascribed to programmer 24 herein, and information used by processor 100 to provide the functionality ascribed to programmer 24 herein. Memory 102 may include any fixed or removable magnetic, optical, or electrical media, such as RAM, ROM, CD-ROM, hard or floppy magnetic disks, EEPROM, or the like. Memory 102 may also include a removable memory portion that may be used to provide memory updates or increases in memory capacities. A removable memory may also allow patient data to be easily transferred to another computing device, or to be removed before programmer 24 is used to program therapy for another patient.

Programmer 24 may communicate wirelessly with IMD 16, such as using RF communication or proximal inductive interaction. This wireless communication is possible through the use of telemetry module 106, which may be coupled to an internal antenna or an external antenna. An external antenna that is coupled to programmer 24 may correspond to the programming head that may be placed over heart 12, as described above with reference to FIG. 1. Telemetry module 106 may be similar to telemetry module 88 of IMD 16 (FIG. 4).

Telemetry module 106 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In this manner, telemetry module 106 may transmit an interrogation request to telemetry module 88 of IMD 16. Accordingly, telemetry module 106 may receive higher resolution diagnostic information or lower resolution diagnostic information selected by the request or based on already entered patient status to IMD 16. The higher resolution diagnostic information may include patient metric values or other detailed information from telemetry module 88 of IMD 16. The lower resolution diagnostic information may include an alert or notification of the heart failure risk level from telemetry module 88 of IMD 16. The alert may be automatically transmitted, or pushed, by IMD 16 when the heart failure risk level becomes critical. In addition, the alert may be a notification to a healthcare professional, e.g., a clinician or nurse, of the risk level and/or an instruction to patient 14 to seek medical treatment for the potential heart failure condition that may require re-hospitalization is left untreated. In response to receiving the alert, user interface 104 may present the alert to the healthcare professional regarding the risk level or present an instruction to patient 14 to seek medical treatment.

Either in response to pushed heart failure information, e.g., the risk level or patient metrics, or requested heart failure information, user interface 104 may present the patient metrics and/or the heart failure risk level to the user. In some examples, user interface 104 may also highlight each of the patient metrics that have exceeded the respective one of the plurality of metric-specific thresholds. In this manner, the user may quickly review those patient metrics that have contributed to the identified heart failure risk level.

Upon receiving the alert via user interface 104, the user may also interact with user interface 104 to cancel the alert, forward the alert, retrieve data regarding the heart failure risk level (e.g., patient metric data), modify the metric-specific thresholds used to determine the risk level, or conduct any other action related to the treatment of patient 14. In some examples, the clinician may be able to review raw data (e.g., higher resolution diagnostic information) to diagnose any other problems with patient 14 or monitor the efficacy of treatments given to patient 14. For example, the clinician may check if the intrathoracic impedance has increased after diuretic therapy or if the heart rate has decreased during atrial fibrillation in response to a rate controlling drug. User interface 104 may even suggest treatment along with the alert, e.g., certain drugs and doses, to minimize symptoms and tissue damage that could result from heart failure. User interface 104 may also allow the user to specify the type and timing of alerts based upon the severity or criticality of the heart failure risk level. In addition to the heart failure risk level, in other examples, user interface 104 may also provide the underlying patient metrics to allow the clinician to monitor therapy efficacy and remaining patient conditions.

In some examples, processor 100 of programmer 24 and/or one or more processors of one or more networked computers may perform all or a portion of the techniques described herein with respect to processor 80, metric detection module 92 and IMD 16. For example, processor 100 or a metric detection module 92 within programmer 24 may analyze patient metrics to detect those metrics exceeding thresholds and to generate the heart failure risk level.

Figure 5:
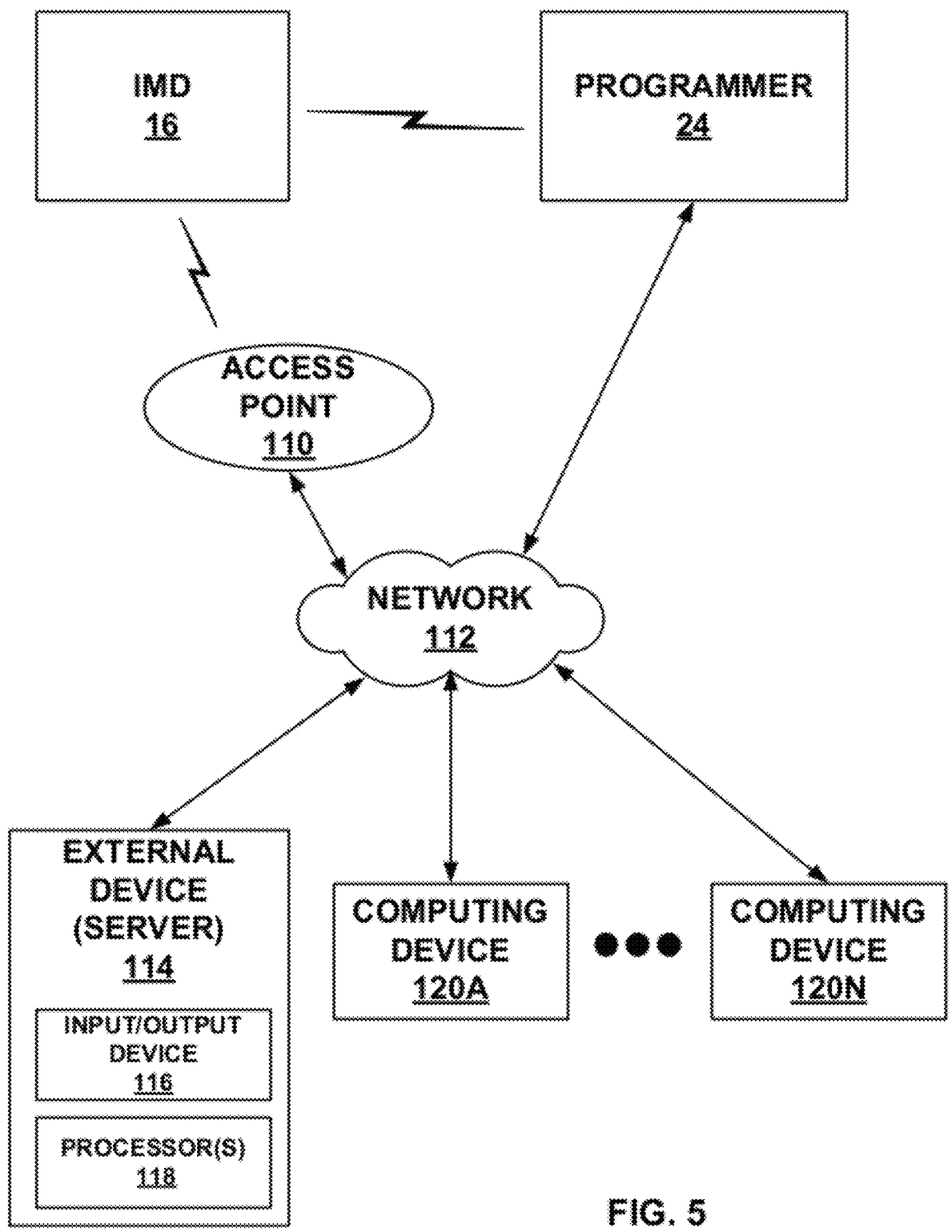
FIG. 5 is a block diagram illustrating an example system that includes an external device, such as a server, and one or more computing devices that are coupled to the IMD and programmer shown in FIG. 1 via a network.

FIG. 5 is a block diagram illustrating an example system that includes an external device, such as a server 114, and one or more computing devices 120A-120N, that are coupled to the IMD 16 and programmer 24 shown in FIG. 1 via a network 112. Network 112 may be generally used to transmit lower resolution diagnostic information (e.g., a risk level) from a remote IMD 16 to another external computing device during a post-hospitalization period. However, network 112 may also be used to transmit higher resolution diagnostic information from IMD 16 to an external computing device within the hospital so that a clinician or other healthcare professional may monitor patient 14. In this example, IMD 16 may use its telemetry module 88 to communicate with programmer 24 via a first wireless connection, and to communication with an access point 110 via a second wireless connection. In the example of FIG. 5, access point 110, programmer 24, server 114, and computing devices 120A-120N are interconnected, and able to communicate with each other, through network 112. In some cases, one or more of access point 110, programmer 24, server 114, and computing devices 120A-120N may be coupled to network 112 through one or more wireless connections. IMD 16, programmer 24, server 114, and computing devices 120A-120N may each comprise one or more processors, such as one or more microprocessors, DSPs, ASICs, FPGAs, programmable logic circuitry, or the like, that may perform various functions and operations, such as those described herein.

Access point 110 may comprise a device that connects to network 112 via any of a variety of connections, such as telephone dial-up, digital subscriber line (DSL), or cable modem connections. In other examples, access point 110 may be coupled to network 112 through different forms of connections, including wired or wireless connections. In some examples, access point 110 may be co-located with patient 14 and may comprise one or more programming units and/or computing devices (e.g., one or more monitoring units) that may perform various functions and operations described herein. For example, access point 110 may include a home-monitoring unit that is co-located with patient 14 and that may monitor the activity of IMD 16. In some examples, server 114 or computing devices 120 may control or perform any of the various functions or operations described herein, e.g., generate a heart failure risk level based on the patient metric comparisons or create patient metrics from the raw metric data.

In some cases, server 114 may be configured to provide a secure storage site for archival of higher or lower resolution diagnostic information (e.g., patient metric data and/or heart failure risk levels) that has been collected and generated from IMD 16 and/or programmer 24. Network 112 may comprise a local area network, wide area network, or global network, such as the Internet. In some cases, programmer 24 or server 114 may assemble the lower or higher resolution diagnostic information in web pages or other documents for viewing by and trained professionals, such as clinicians, via viewing terminals associated with computing devices 120. The system of FIG. 5 may be implemented, in some aspects, with general network technology and functionality similar to that provided by the Medtronic CareLink® Network developed by Medtronic, Inc., of Minneapolis, Minn.

In the manner of FIG. 5, computing device 120A or programmer 24, for example, may be remote computing devices that receive and present lower resolution diagnostic information transmitted from IMDs of multiple patients so that a clinician may prioritize the patients needing treatment immediately. In other words, the clinician may triage patients by analyzing the heart failure risk levels of multiple patients. The computing device may use its communication module to receive the lower resolution diagnostic information (e.g., heart failure risk levels) transmitted from multiple IMDs via network 112. In this manner, each heart failure risk level is representative of one the patients. Although the IMDs may transmit the lower resolution diagnostic information at any time, generally the IMDs may transmit lower resolution diagnostic information on a daily basis or in response to an interrogation request from an external computing device. In other examples, the IMDs may be configured to transmit lower resolution diagnostic information when the risk level becomes critical or there is a medium or high risk of re-hospitalization within a predetermined period. A processor within the remote computing device may then automatically rank each of the patients based on each of the heart failure risk levels and the user interface may present the list of ranked patients to the clinician. Generally, the list will start with the most critical patient, e.g., the highest risk level, at the top. This method may be useful for healthcare professionals making house calls, serving patients within a nursing home, or any other circumstance in which a professional treats many patients. The healthcare professionals may thus triage patients in order to minimize any re-hospitalization due to heart failure.

Figure 6:
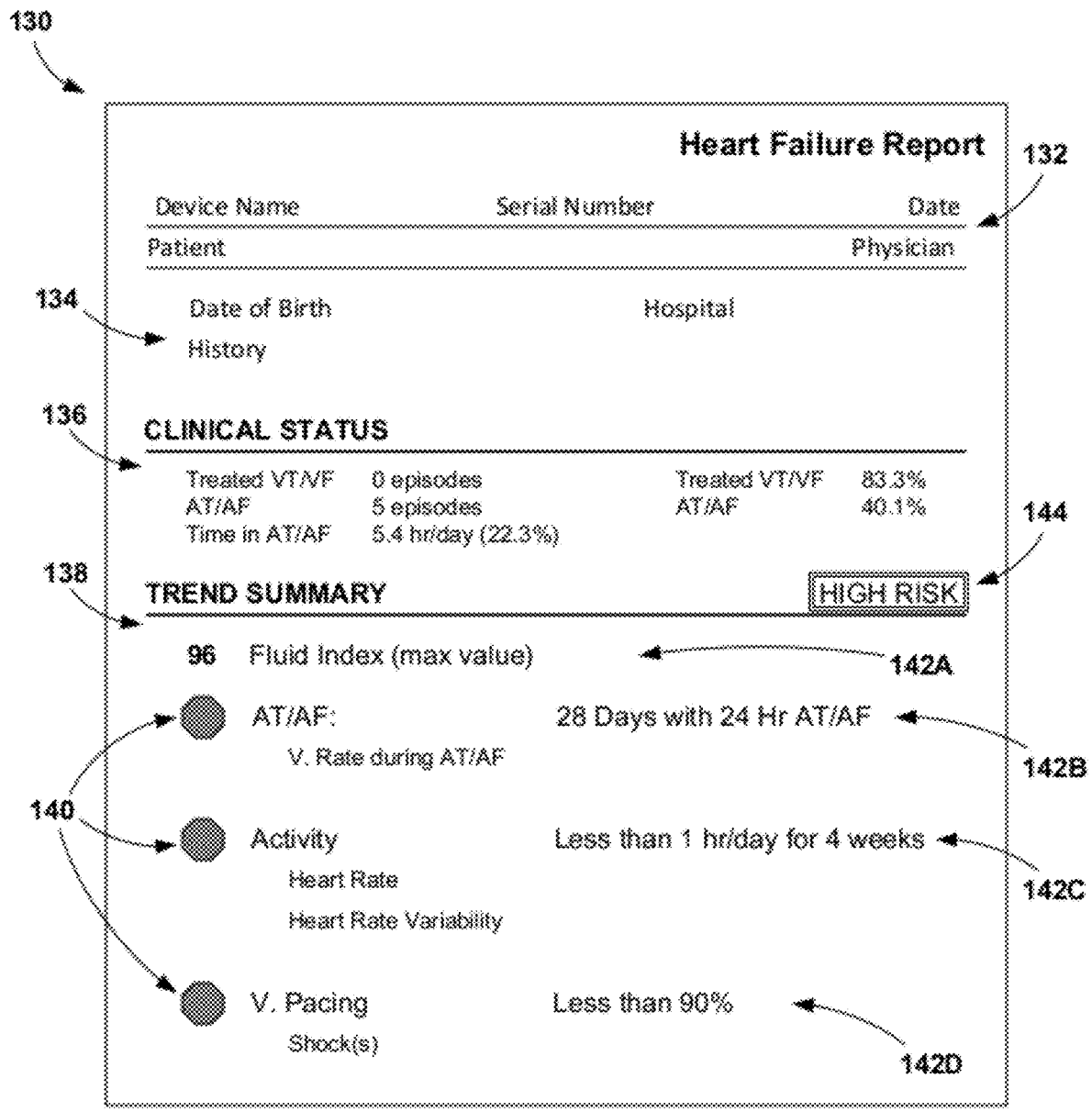
FIG. 6 illustrates an example user interface that includes a risk level that indicates a risk of the patient for hospitalization due to heart failure.

FIG. 6 illustrates an example screen 130 of user interface 104 that includes lower resolution diagnostic information. As shown in FIG. 6, screen 130 includes risk level 144 that indicates the risk that patient 14 will be hospitalized due to heart failure. As described herein, the heart failure risk level may be indicative that patient 14 would be hospitalized for a first time or hospitalized for another time (e.g., re-hospitalized or re-admitted). Although screen 130 is described as being presented on user interface 104 of programmer 24, screen 130 may be presented on any user interface of any device used by a healthcare professional. The heart failure report of screen 130 may be transmitted to a user at a scheduled frequency, e.g., once a day or once a week, or in response to an interrogation request from the user. As shown in FIG. 6, screen 130 is a heart failure report that includes identification data 132 and patient history data 134. Identification data 132 includes items such as the patient name, the device name, the serial number of IMD 16, the date, and even the physician name. Patient history data 134 may be relevant data that may help in the treatment of patient 14.

Screen 130 also includes clinical status 136 that includes information regarding the stimulation therapy delivered by IMD 16. Screen 130 also presents trend summary 138. Trend summary 138 presents a snapshot of certain patient metrics that are exceeding their respective metric thresholds to contribute to the severity of heart failure risk level 144. Critical indicator 140 is provided to remind the user that each of the patient metrics with critical indicator 140 is contributing to the heart failure risk level because the metric threshold has been met or exceeded. In examples in which risk level 144 is determined with a statistical analysis, critical indicator 140 may not be necessary. However, certain patient metrics that contribute significantly to the probability that patient 14 may be re-hospitalized may still be presented to the user.

In the example of FIG. 6, trend summary 138 presents four patient metrics 142A, 142B, 142C, and 142D (collectively "patient metrics 142"). Thoracic fluid index metric 142A indicates a maximum detected value of 96. Although thoracic fluid index metric 142A is not contributing to risk level 144 in this example, it is provided because it is an important indicator of thoracic fluid volume and potential heart failure. Atrial fibrillation duration 142B indicates that patient 14 has had 28 days of atrial fibrillation or atrial tachycardia for 24 hours. Activity metric 142C indicates that patient 14 has been active for less than 1 hour per day for the last 4 weeks. In addition, ventricular pacing metric 142D (e.g., a cardiac resynchronization therapy percentage) indicates that IMD 16 has been pacing heart 12 less than 90 percent of the time. As patient metrics 142 indicate, information may be given that is more specific than just a threshold has been exceeded. The actual observed patient metric data, or summary of the data, may be presented in trend summary 138.

Since each of patient metrics 142B-D has exceeded their respective metric-specific threshold, critical indicator 140 is provided for each metric. The user then knows that heart failure risk level 144 is generated with these critical patient metrics. Also, risk level 144 indicates that patient 14 is at "high risk" for being admitted to the hospital for heart failure. As described herein, risk level 144 may have two or more levels that indicate the severity of heart failure for patient 14. In some examples, "low risk" may indicate that no patient metrics have exceeded their respective metric-specific threshold, "medium risk" may indicate that one patient metric has exceeded their respective metric-specific thresholds, and "high risk" may indicate that two or more patient metrics have exceeded their respective metric-specific thresholds. Since three patient metrics, e.g., patient metrics 142B-D, have exceeded their respective metric-specific thresholds, risk level 144 is indicated as "high risk" in this example.

Risk level 144 is highlighted by a double-lined rectangle for easy location by the user. In other examples, risk level 144 may stand out from the rest of screen 130 in different manners. For example, risk level 144 may be of a different color, font size, or be presented with animation (e.g., flashing or scrolling). Alternatively, risk level 144 may be located at the top of screen 130 or other easily identifiable location. Although heart failure risk level 144 is generally presented as a word category, risk level 144 may be presented with a fraction, percentage, weighted average, or other numerical score that indicates that the severity of the heart failure risk level. For example, risk level 144 may be provided as a fraction of the critical patient metrics over the total number of observed patient metrics to give the user an immediate indication of the severity of the heart failure.

Risk level 144 and patient metrics 142 may be considered lower resolution diagnostic information. This data of screen 130 may be lower resolution because it is transmitted to the user at a low frequency, e.g., once per day or less, or it includes data detected and stored at a low frequency, e.g., once a day or less. In other examples, lower resolution diagnostic information may include risk levels or patient metrics transmitted or detected more frequently. However, lower resolution diagnostic information may still be transmitted less frequently or with less detail than that of higher resolution diagnostic information. Lower resolution diagnostic information may have less detail than the higher resolution diagnostic information because the lower resolution information may be a generated value, metric, or risk level from raw data. In other words, the lower resolution diagnostic information may include a simplified indication of the patient risk than would otherwise be present in the raw data acquired from the patient.

Although screen 130 may be a passively presented informational screen, screen 130 may be interactive. The user may select areas of screen 130 to view more details about any of patient metrics 142, e.g., the user may request higher resolution diagnostic information from IMD 16. Screen 130, in other examples, may provide scroll bars, menus, and navigation buttons to allow the user to view additional information, adjust therapy, adjust metric parameters, or perform other operations related to the treatment of patient 14 with the patient metrics and risk level.

In other examples, risk level 144 may be transmitted in a different manner. In other words, the lower resolution diagnostic information may be transmitted without additional extraneous data such as patient metrics 142. For example, risk level 144 may be transmitted as a single data point associated with the name of patient 14. Alternatively, risk level 144 may be transmitted to a remote computing device as a data point and the remote computing device may update the risk level for that particular patient. In other examples, risk level 144 may be transmitted as part of a text message, electronic mail message, or other formatted message to a mobile computing device carried by a clinician or healthcare professional. After the user receives the lower resolution diagnostic information, the user may send an interrogation request to IMD 16 for additional information, e.g., higher resolution diagnostic information.

Figure 7:
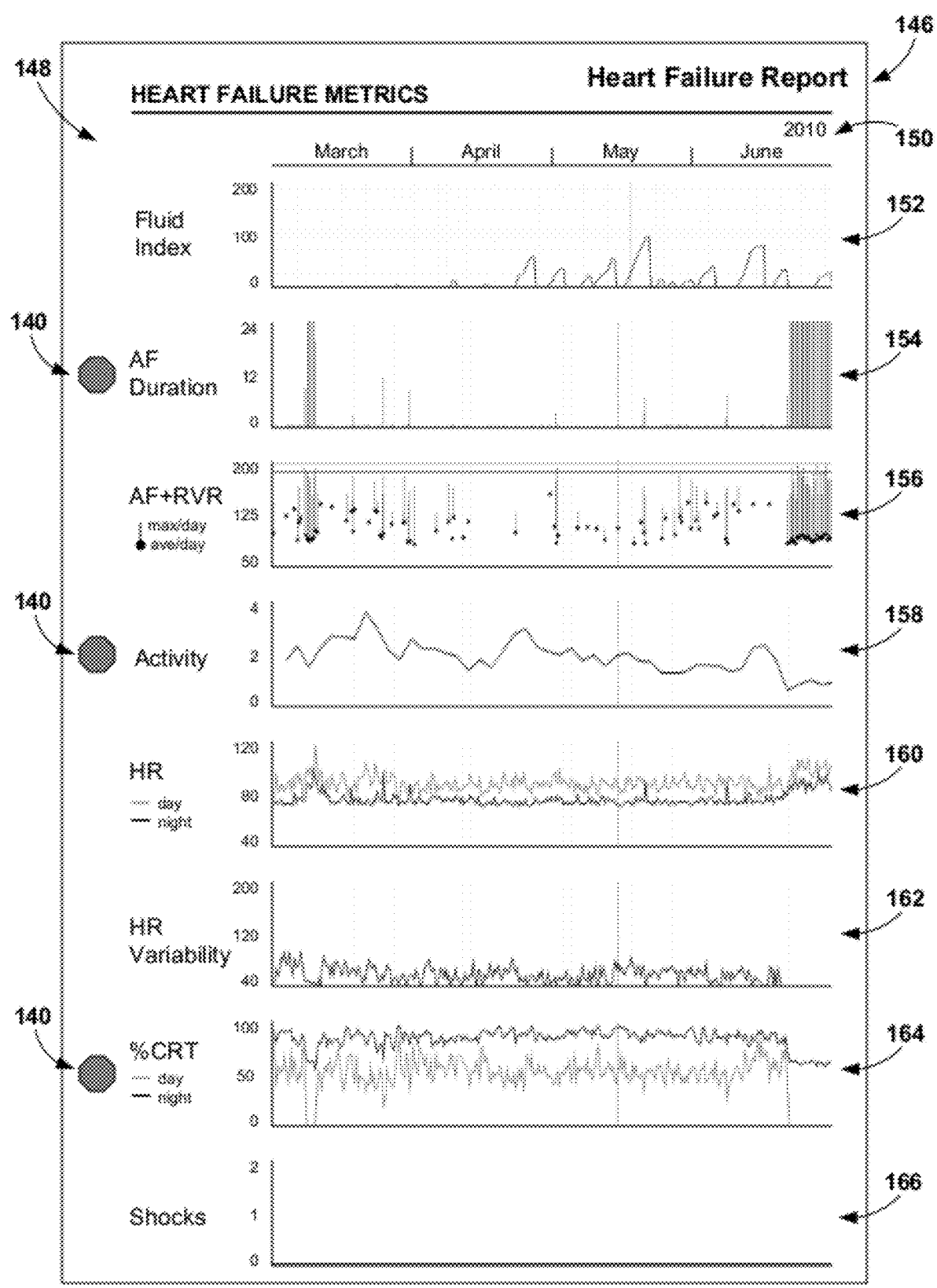
FIG. 7 illustrates an example user interface that includes diagnostic information from a plurality of patient metrics used to generate the heart failure risk level.

FIG. 7 illustrates an example screen 146 of user interface 104 that includes higher resolution diagnostic information. Screen 146 may include data (e.g., raw or calibrated data) from all of the patient metrics used to generate the heart failure risk level for patient 14. Since screen 146 includes data collected from patient 14, screen 146 includes higher resolution diagnostic information than the information of screen 130 of FIG. 6. Although screen 146 is described as being presented on user interface 104 of programmer 24, screen 130 may be presented on any user interface of any device used by a healthcare professional. As shown in FIG. 7, screen 146 provides another heart failure report, similar to screen 130 of FIG. 6. However, screen 146 provides higher resolution diagnostic information of heart failure metrics 148 that include those patient metrics used to generate the heart failure risk level. Included are the metric data for eight patient metrics 152, 154, 156, 158, 160, 162, 164, and 166. Timeline 150 indicates for which months the data is representative in all the metric graphs. Although this four month period may be the evaluation window, timeline 150 may cover many evaluation windows. For example, the evaluation window may be equal to one week or one month, such that the risk level is reviewed after the evaluation window expires. In addition, the user may move through time with an interactive timeline 150 in other examples. Although not presented in screen 146, the heart failure risk level may also be presented. In some examples, the user may select any point within the graphs for the patient metrics to retrieve specific values of the patient metric at that point in time.

Thoracic fluid index metric 152 is labeled as "Fluid Index." Thoracic fluid index metric 152 illustrates that the thoracic fluid index has been periodically raising and lowering over the months of May and June. In one example, the thoracic fluid index threshold may be approximately 60. However, the thoracic fluid index threshold may be generally between approximately 40 and 200.

Atrial fibrillation duration metric 154 is labeled "AF Duration" and indicates how many hours each day that the patient endured atrial fibrillation. As shown, atrial fibrillation duration metric 154 includes critical indicator 140 because of the days of atrial fibrillation shown at the end of June. An example atrial fibrillation duration threshold may be approximately 6 hours. However, the atrial fibrillation duration threshold may be set generally between approximately 1 hour and 24 hours.

Ventricular contraction metric 156 is labeled "AF+RVR" and indicates the ventricular contraction rate during atrial fibrillation. The graph of ventricular contraction metric 156 provides the average ventricular contraction rate for each day and also the maximum ventricular contraction rate observed during each day. Generally, the ventricular contraction rate during atrial fibrillation threshold may be set between approximately 70 beats per minute and 120 beats per minute for 24 hours. In one example, the ventricular contraction rate threshold may be approximately equal to 90 beats per minute for 24 hours. In other examples, the duration of 24 hours may be shorter or longer.

Activity metric 158 also is highlighted with critical indicator 140. Activity metric 158 is labeled "Activity" and indicates for how many hours the patient is active each day. A patient may be considered active when, for example, the output of an accelerometer exceeds a threshold. Lower activity levels may be a risk factor for heart failure, and the graph of activity metric 158 indicates that patient 14 has been less active at the end of June. In this manner, the patient metric of activity may be a metric where exceeding the metric-specific threshold includes dropping below the threshold. In one example, the patient activity threshold may be approximately equal to 1 hour per day for seven consecutive days. In other examples, the threshold may be set to more or less time over a different duration. Instead of hours per day, other examples of activity metric 158 may provide durations of certain postures, e.g., lying down, sitting up, or standing. In general, activity metric 158 may include measurements of the rigor of patient activity and/or the amount of time patient 14 is active.

Screen 148 also provides for heart rate metrics. Heart rate metric 160 is labeled "HR" and indicates separate graphs for each of the nighttime heart rate and daytime heart rate. In some examples, the nighttime heart rate may be more indicative of heart failure risk. Generally, the nighttime hear rate threshold may be set to between approximately 70 beats per minute and 120 beats per minute for a certain period of time. In one example, the nighttime heart rate threshold may be approximately 85 beats per minute for seven consecutive days. Heart rate variability metric 162 is labeled "HR Variability" and indicates the degree of change in heart rate throughout the day. Since lower heart rate variability may indicate an increased sympathetic tone detrimental to blood flow through the vasculature, heart rate variability may also be a patient metric where exceeding the metric-specific threshold includes dropping below the threshold. In one example, the heart rate variability threshold may be set to approximately 40 milliseconds for seven consecutive days, but other variability thresholds may also be used. In other examples, screen 148 may also provide comparisons between two or more patient metrics, e.g., the difference between day heart rate and nighttime heart rate.

In addition, screen 148 may also provide a few patient metrics derived from therapy delivered to patient 14. Therapy percentage metric 164 is labeled "% CRT" and indicates the percentage of time each day and night that IMD 16 is delivering a cardiac resynchronization therapy, e.g., pacing therapy. Lower percentages of therapy may indicate diminished blood flow through the vasculature. Generally, the cardiac resynchronization therapy percentage threshold may be set to a value between 70 percent and 100 percent for a given period of time. In one example, the cardiac resynchronization therapy percentage threshold may be set to approximately 90 percent for five of seven consecutive days. Since the nighttime therapy percentage is less than 90 percent, critical indicator 140 is used to highlight therapy percentage metric 164.

In other examples, a ventricular pacing percentage may be monitored for patients receiving pacing therapy with dual or single chamber pacing devices. Increased ventricular pacing from single chamber cardiac resynchronization therapy devices may increase the risk of heart failure in some patients due to desynchronization of ventricular contractions in the heart. Conversely, lower ventricular pacing in dual chamber devices may increase the risk of heart failure in some patients.

Further, shock metric 166 is labeled "Shocks" and indicates the number of electrical shock events, e.g., cardioversion or defibrillation, endured by patient 14. As shown in FIG. 7, patient 14 has not been subjected to any shock therapy. Although the threshold may be set to a different value, the electrical shock threshold may generally be set to approximately 1 electrical shock.

Since each of patient metrics 154, 158, and 164 have exceeded their respective metric-specific threshold, critical indicator 140 is provided for each metric. In addition to, or in place of, critical indicators 140, patient metrics may be highlighted with a different text color, circles or boxes surround each metric, or some other indication of the critical level of each metric. In other examples, other patient metrics may be presented in heart failure metrics 148, e.g., blood pressure, blood glucose, lung volume, lung density, or respiration rate, weight, sleep apnea burden derived from respiration, temperature, ischemia burden, sensed cardiac event intervals, and troponin and/or brain natriuretic peptide (BNP) levels.

Although screen 148 may be a passively presented informational screen with higher resolution diagnostic information, screen 148 may be interactive. The user may select areas of screen 148 to view more details about any of the presented patient metrics, for example. The user may also move to different time periods with timeline 150. Screen 130, in other examples, may provide scroll bars, menus, and navigation buttons to allow the user to view additional information, adjust therapy, adjust metric parameters, or perform other operations related to the treatment of patient 14 with the patient metrics and risk level. Further, the user may interact with the graph of each patient metric to expand the graph and view more details of the graph, perhaps even individual values.

In other examples, higher resolution diagnostic information may be presented one patient metric at a time or even raw data that IMD 16 uses to generate the patient metric. For example, during a hospitalization period for patient 14, IMD 16 may transmit the detected thoracic impedances to a remote computing device of a clinician treating patient 14. IMD 16 may transmit detected thoracic impedances at a predetermined interval or in response to an interrogation request from the clinician. The predetermined interval may be generally between approximately one minute and four hours, but other predetermined intervals may be used. The clinician may use some or all of the higher resolution diagnostic information to determine when patient 14 has improved enough to be discharged from a hospital setting, or whether patient 14 should be admitted to the hospital due to heart failure.

Figure 8:
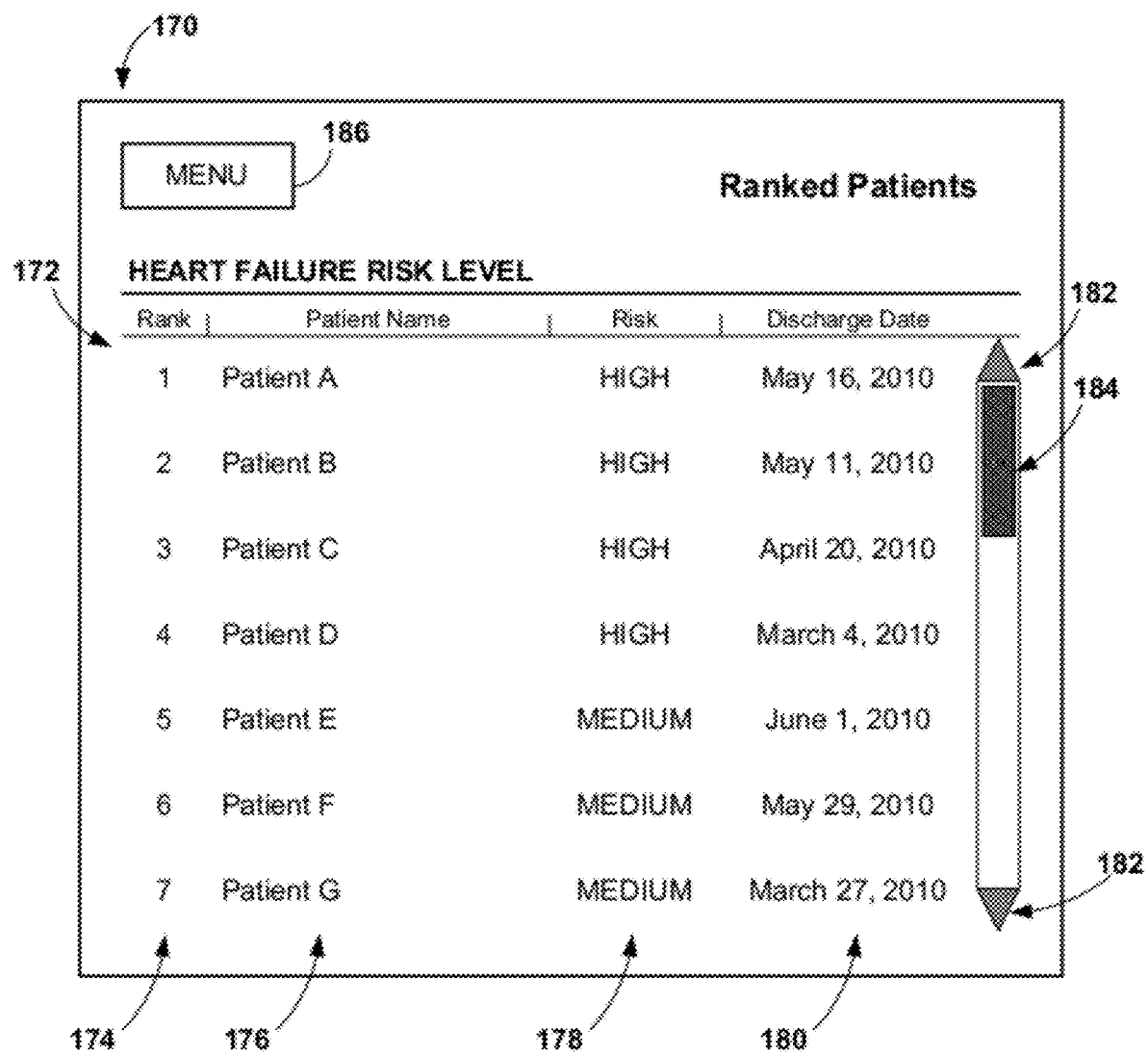
FIG. 8 illustrates an example user interface that includes a list of patients ranked by the risk level for hospitalization due to heart failure.

FIG. 8 illustrates example user interface 170 that includes a list 172 of patients 176 ranked by the risk level 178 for hospitalization due to heart failure. In other words, user interface 170 may be used when remotely monitoring non-hospitalized patients. User interface 170 may be a user interface of an external computing device, but user interface 170 may also be an example of user interface 104 of programmer 24 if programmer 24 is capable of receiving the lower resolution diagnostic information of risk levels from multiple patients.

As shown in the example of FIG. 8, user interface 170 presents list 172 of patients being monitored by the clinic or clinician. The risk level 178 of each patient may be different.

A communication module of the computing device has already received the risk levels from the IMDs of multiple patients and the processor has automatically ranked the patients by risk level. Although list 172 may include patients with a low risk level (not shown in FIG. 8), only patients with high or medium risk of re-hospitalization may be provided in other examples.

User interface 170 includes list 172, scroll arrows 182, scroll bar 184, and menu 186. The user may select either of scroll arrows 182 to navigate through list 172 or select and move scroll bar 184 to navigate to other portions of list 172 not shown within the viewable field of the list. List 172 includes four data fields. Rank 174 indicates the severity of the risk level for each patient, patients 176 includes the name of each patient in the list, risk levels 178 provides the received heart failure risk level for each patient, and visit date 180 provides the date of the last visit between the patient and a healthcare professional.

As shown in the example of FIG. 8, the patient "Patient A" has been ranked first because he has a "high risk" level and he was discharged from the hospital the most recently. This may indicate that he is worsening faster than the other "high risk" patients. Alternatively, patients with the same risk level may be further ranked by the number of patient metrics exceeding their respective specific metric thresholds, the last time each patient has been examined by a clinician, or any other factors. List 172 thus allows a healthcare professional to triage patients and give attention to the patients most needing the treatment. In other examples, list 172 may be presented one patient at a time. In other words, user interface 170 may force the user to view the most at risk patients first, one at a time.

Generally, screen 170 provides lower resolution diagnostic information for each of patients 174. However, the user may select a specific patient to submit an interrogation request for higher resolution diagnostic information from the IMD of that patient. In this manner, the clinician may remotely investigate the situation of the patient before personally visiting the patient or requesting that the patient be admitted to a hospital.

Figure 9:
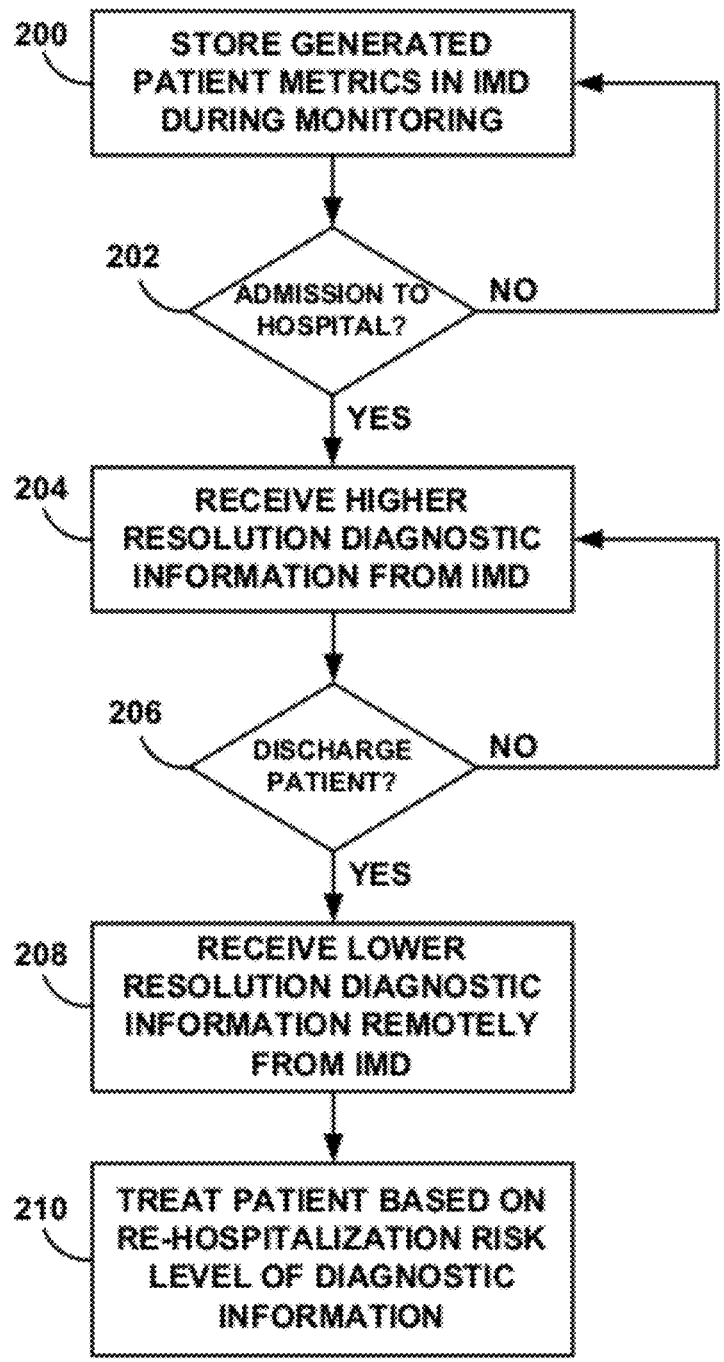
FIG. 9 is a flow diagram of an example technique for treating a patient based on diagnostic information stored by the IMD.

FIG. 9 is a flow diagram of an example technique for treating a patient based on diagnostic information stored by the IMD. The example of FIG. 9 is described with respect to patient 14, IMD 16, and a clinician. However, other patients, IMDs, or healthcare professionals may be described in this technique. Initially, IMD 16 is implanted in patient 14 to perform therapy and/or monitoring functions. During monitoring functions, IMD 16 generates (or detects) one or more patient metrics and stores these patient metrics in memory 82 during monitoring (200). IMD 16 may store patient metrics for only a certain amount of time, but old patient metrics may be archived outside of IMD 16 in other examples. This period may be described as pre-hospitalization monitoring.

Once patient 14 arrives at the emergency room or the clinician considers admitting patient 14 to the hospital, the clinician may interrogate IMD 16 for diagnostic information related to heart failure of patient 14 and determine if patent 14 should be admitted to the hospital (202). This admission decision may include multiple steps. For example, the clinician may send an interrogation request to IMD 16 and receive transmitted higher resolution diagnostic information from IMD 16. The clinician may then look back at this diagnostic information stored in IMD 16 to identify medical problems with patient 14. The clinician may also incorporate other clinical measures or diagnostics taken of patient 14 with the higher resolution diagnostic information to make a diagnostic decision on patient 14. From this diagnostic decision, the clinician, or other healthcare professional, may determine if patient 14 should be admitted to the hospital. If patient 14 is not admitted to the hospital ("NO" branch of block 202), then IMD 16 may continue monitoring patient 14.

If patient 14 is admitted to the hospital ("YES" branch of block 202), then a computing device within the hospital receives higher resolution diagnostic information from IMD 16 during the hospitalization period (204). The higher resolution diagnostic information may include, for example, one or more of thoracic impedance values, atrial fibrillation after cardioversion, changes to heart rate variability, changes of ventricular heart rates during a persistent atrial fibrillation resulting from a Beta-blocker therapy, or changes of night heart rate due to increased angiotensin-converting enzyme (ACE) inhibitor therapy, or increases in intrathoracic impedance due to diuretic therapy. The clinician may review the higher resolution diagnostic information and evaluate the efficacy of currently delivered therapies during hospitalization. The clinician may then make necessary changes to patient treatment during hospitalization. The higher resolution diagnostic information transmitted by IMD 16 may provide patient metrics not easily detectable by non-invasive techniques normally available in the hospital setting.

The clinician may also use the higher resolution diagnostic information to determine when discharge of patient 14 is appropriate (206). If the diagnostic information does not indicate that patient 14 should be discharged from the hospital, e.g., end the hospitalization period ("NO" branch of block 206), IMD 16 may continue to transmit the higher resolution diagnostic information to the clinician. If the diagnostic information suggests that patient 14 has improved enough to be discharged from the hospital ("YES" branch of block 206), then patient 14 is discharged. For example, if the clinician determines that the thoracic impedance of patient 14 has increased sufficient to suggest that heart failure is not longer of immediate concern, the clinician may end the hospitalization period.

Once the hospitalization period has ended, IMD 16 may begin operating during a post-hospitalization period in which IMD 16 remotely transmits lower resolution diagnostic information that is received by the clinician (200). IMD 16 may switch to lower resolution diagnostic information transmission upon receiving a first remote interrogation request or other command that indicates patient 14 has been discharged from the hospital. As described herein, IMD 16 may transmit a heart failure risk level and/or other less frequent or less detailed patient metrics. The clinician may receive the lower resolution diagnostic information periodically from IMD 16 or after submitting an interrogation request for the information.

Based on the risk level transmitted to the clinician in the lower resolution diagnostic information, the clinician may treat patient 14 (210). As described herein, the lower resolution diagnostic information may include a risk level that the patient may need to be re-hospitalized within a predetermined period. This predetermined period may be on the order of days, weeks, or months (e.g., approximately 30 days). After receiving the remote transmission of lower resolution diagnostic information, the clinician may determine the best course of action. In some examples, the clinician may request more detailed diagnostic information to make a diagnosis of patient 14. Based on the transmitted information (e.g., a high risk level), the clinician may contact patient 14 to make treatment modifications or other changes to the lifestyle of patient 14 to reduce the severity of heart failure. In this manner, the clinician may attempt to prevent patient 14 from being re-hospitalized due to heart failure. If patient 14 is needed to be re-hospitalized, the clinician may again determine if patient 14 needs to be admitted to the hospital (202).

Figure 10:
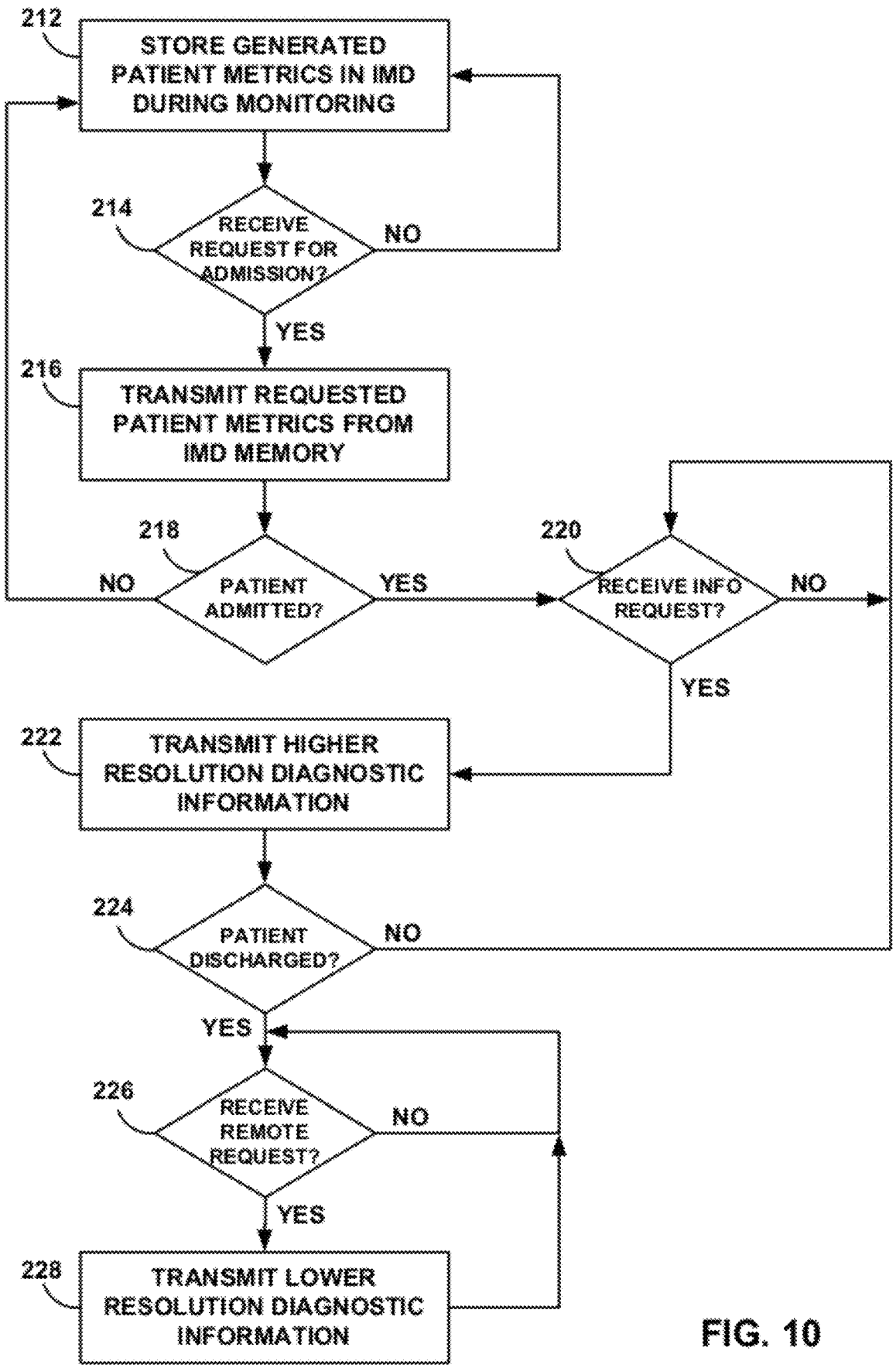
FIG. 10 is a flow diagram of an example technique for transmitting patient metrics and diagnostic information from an IMD.

FIG. 10 is a flow diagram of an example technique for transmitting patient metrics and diagnostic information from IMD 16. After initial implantation, IMD 16 may generally be operated in a monitoring mode with or without delivering therapy. During this monitoring mode, IMD 16 automatically detects (or generates) patient metrics related to heart failure and stores them in memory 82 (212). These patient metrics may be accessed by a clinician or other healthcare professional as needed to provide effective treatment to patient 14. As long as IMD 16 does not receive an interrogation request for admission to a hospital ("NO" branch of block 214), IMD 16 continues to store detected patient metrics (212).

If IMD 16 does receive an interrogation request for admitting patient 14 to a hospital ("YES" branch of block 214), IMD 16 transmits the requested patient metrics from memory 82 within IMD 16 (216). In some examples, the patient metrics may be transmitted as higher resolution diagnostic information, e.g., patient metric values over a previous time period. In other examples, IMD 16 may transmit lower resolution diagnostic information, e.g., a heart failure risk level and/or a single recent patient metric value. IMD 16 may transmit lower resolution diagnostic information to emergency personnel not familiar with individual patient metrics, but higher resolution diagnostic information may be transmitted to a clinician that in trained in making a treatment/admission decision based on the patient metrics. If patient 14 is not admitted to the hospital ("NO" branch of block 218), IMD 16 may revert back to the previous monitoring mode (212).

If patient 14 is admitted to the hospital ("YES" branch of block 218), IMD 16 waits to receive a higher resolution diagnostic information interrogation request (220). This interrogation request may be a command from programmer 24 or another remote computing device that requests one or more patient metric values or raw data that is used to generate the patient metric. Once IMD 16 receives the interrogation request ("YES" branch of block 220), IMD 16 transmits higher resolution diagnostic information to programmer 24, for example (222). The higher resolution diagnostic information may be used by the clinician to make a discharge decision, in addition to making necessary adjustments for treatment. If the hospitalization period continues because patient 14 has not been discharged from the hospital ("NO" branch of block 224), IMD 16 continues to wait for another interrogation request from the clinician. In other examples, IMD 16 may periodically transmit the higher resolution diagnostic information without first receiving an interrogation request. In this manner, IMD 16 may be programmed to periodically detect and transmit the most recent higher resolution diagnostic information during the hospitalization period.

If patient 14 has been discharged from the hospital ("YES" branch of block 224), IMD 16 enters a post-hospitalization period and waits to receive a remote interrogation request for diagnostic information (226). Once IMD 16 receives the remote interrogation request ("YES" branch of block 226), IMD 16 transmits lower resolution diagnostic information to the remote computing device that requested the information (228). As described herein, the lower resolution diagnostic information may include a risk level that identify patient 14 is at risk of being re-hospitalized for heart failure. The lower resolution diagnostic information may include a risk level based on patient metrics detected over the previous predetermined period, e.g., one day, seven days, or one month. In this manner, the predetermined period may determine how long a detected patient metric is useful in generating an accurate risk level. In one example, the risk level may only be based on a predetermined period of one week (e.g., the most recent seven day period). In other examples, the lower resolution diagnostic information may include other general patient metric values or latest trends in the patient metrics. IMD 16 then continues to wait until another remote interrogation request is received.

Alternatively, IMD 16 may transmit lower resolution diagnostic information without first receiving an interrogation request. Once IMD 16 is placed into post-hospitalization mode, IMD 16 may periodically transmit lower resolution diagnostic information to a remote computing device. For example, IMD 16 may transmit updated lower resolution diagnostic information once a day, once every other day, once a week, or some other regularly scheduled frequency. Alternatively, IMD 16 may transmit the lower resolution diagnostic information in response to an elevated severity of the heart failure risk level. For example, IMD 16 may immediately transmit the risk level if the risk level has increased from medium risk of re-hospitalization to high risk of re-hospitalization. In other examples, IMD 16 may also transmit higher resolution diagnostic information to a user if the higher resolution diagnostic information is remotely requested based on the transmitted lower resolution diagnostic information.

IMD 16 may continue to automatically detect and store patient metrics regardless of whether IMD 16 is transmitting higher resolution diagnostic information or lower resolution diagnostic information. In one example, IMD 16 may detect and store patient metrics at the same rate (e.g., every minute, hour, or day) independent of whether IMD 16 is transmitting higher or lower resolution diagnostic information. IMD 16 may simply use the stored patient metrics relevant to the type of information being transmitted to the user. In other examples, however, IMD 16 may change the rate of metric detection and/or storage based on whether higher or lower resolution diagnostic information is being transmitted. For example, IMD 16 may detect and store patient metrics less frequently during the lower resolution diagnostic information transmission of the post-hospitalization period because the risk level generation does not require frequent metric detection. Conversely, IMD 16 may increase the frequency of metric detection and storage to satisfy the requirements of the higher resolution diagnostic information transmissions.

Figure 11:
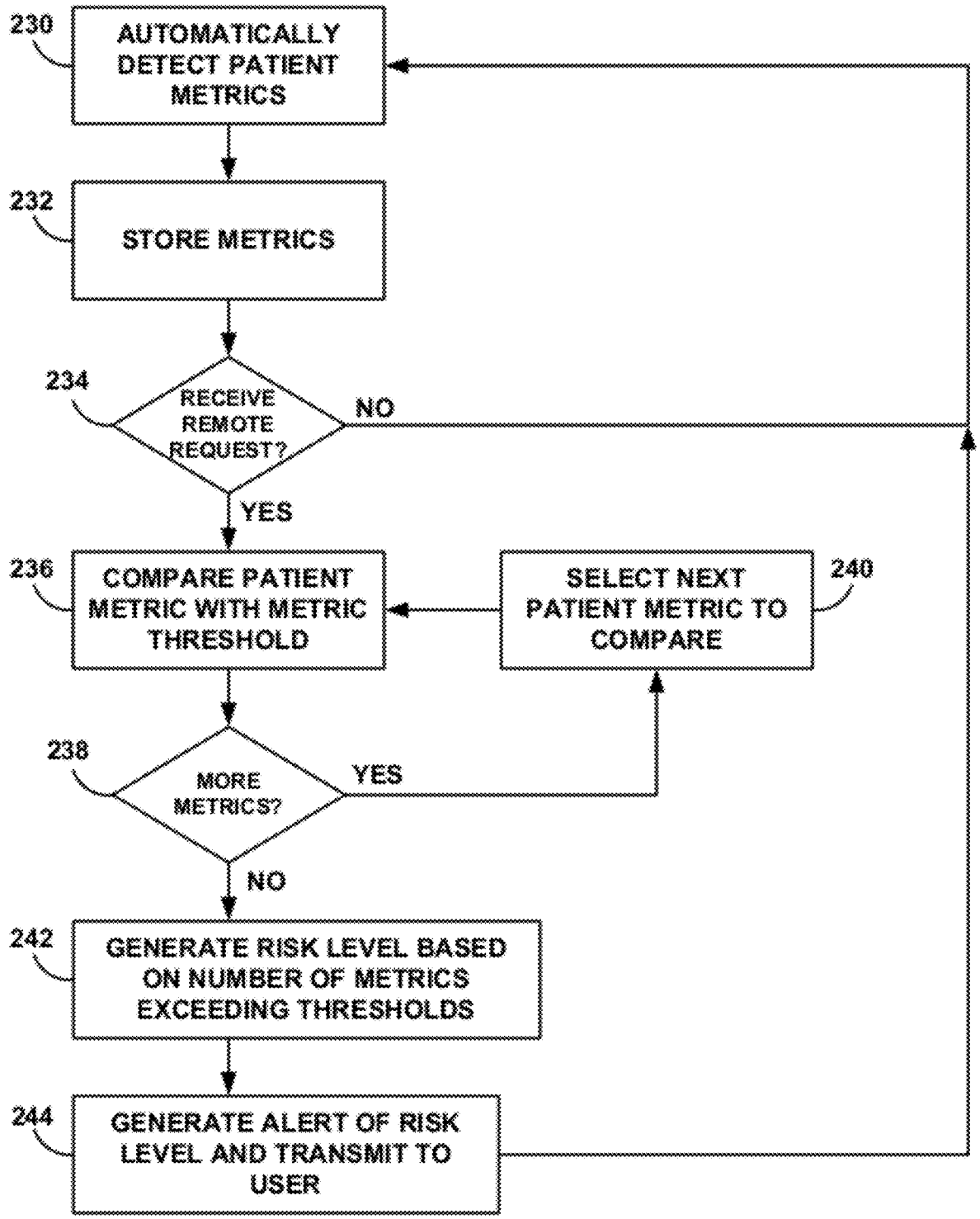
FIG. 11 is a flow diagram of an example technique for generating heart failure risk levels from patient metrics.

FIG. 11 is a flow diagram of an example technique for generating lower resolution diagnostic information, e.g., heart failure risk levels, from patient metrics. FIG. 11 will be described with IMD 16 both detecting patient metrics and generating heart failure risk levels for the patient, but other examples of the same technique may be applied to other devices (e.g. programmer 24 or an external computing device).

As shown in FIG. 11, metric detection module 92 automatically detects the patient metrics from various electrodes, sensors, and therapy information (230). Metric detection module 92 then stores the patient metrics in metric data 85 of memory 82 (232). If processor 80 does not need to generate the heart failure risk level ("NO" branch of block 204), metric detection module 92 continues to detect patient metrics (230). In some examples, processor 80 may only generate the risk level after an evaluation window expires.

For example, if the evaluation window is seven days, processor 80 may only generate the risk level after the seven day period expires. However, processor 80 may generate and transmit the risk level as frequently as every hour or as infrequently as several months. If processor 80 is to generate the heart failure risk level ("Yes" branch of block 234), processor 80 compares one of the patient metrics with the metric-specific threshold of that metric (236). If there are more patient metrics to compare ("Yes" branch of block 238), processor 80 selects the next patient metric to compare (240) and compares the metric to its threshold (236).

Once there are no more patient metrics to compare ("NO" branch of block 208), processor 80 generates the heart failure risk level based on the number of metrics exceeding their thresholds as determined in the comparison step (242). For example, no metrics exceeding their thresholds may be a "low risk" level, one metric exceeding its threshold may be a "medium risk" level, and two or more metrics exceeding their thresholds may be a "high risk" level. In other examples, the risk level may be generated as a fraction, percentage, or other value that represents the number of metrics exceeding their values. In some examples, metric detection module 92 may generate the risk levels with a statistical analysis of the patient metric values instead of using the number of metrics exceeding a threshold.

Once the risk level is generated, processor 80 generates an alert of the risk level and transmits the alert to the user via telemetry module 88 (244). As described herein, the alert may be transmitted on a schedule or as soon as communication is possible to another device or access point. In some examples, the heart failure risk level may only be transmitted when requested by a user. In some examples the alert may also include more detailed information regarding the patient metrics included in the risk level.

Figure 12:
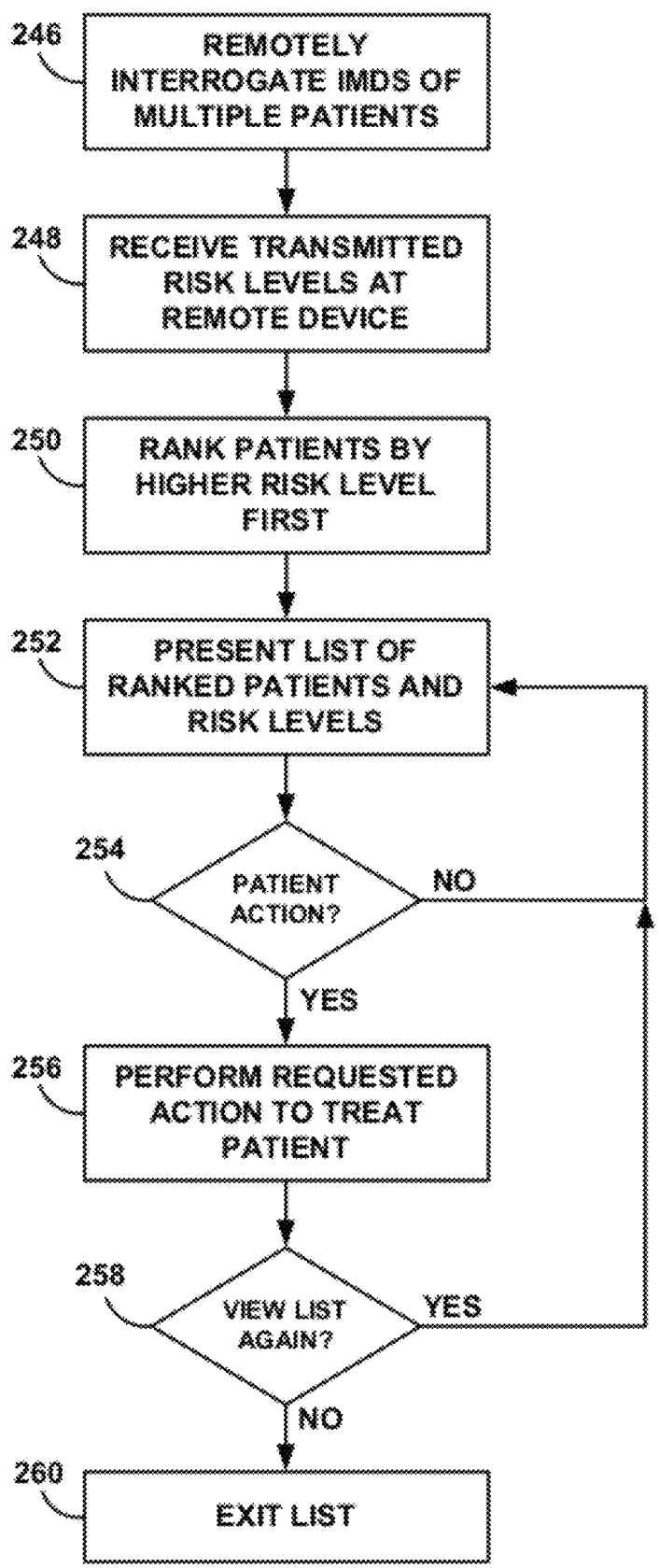
FIG. 12 is a flow diagram of an example technique for presenting a user with a ranked list of patients based on the heart failure risk level of each patient.

FIG. 12 is a flow diagram of an example technique for presenting a user with a ranked list of patients based on the heart failure risk level of each patient. Although the technique of FIG. 12 is generally directed to an external computing device remote of patient 14 (e.g., a networked server, a remote clinician workstation, and/or a clinician mobile device), the technique may be implemented by any device capable of receiving heart failure risk levels from IMDs of multiple patients. As shown in FIG. 12, the external computing device remotely interrogates the IMD for each patient in the care of the user (246). The external computing device then receives the transmitted risk levels (or other lower resolution diagnostic information) from each IMD (248). However, in other examples, each IMD may independently transmit (or push) alerts at a predetermined or scheduled time, when risk levels change, or when heart failure risk levels are at or above a certain severity.

The computing device processor next analyzes the heart failure risk levels and ranks each patient by the highest, or most critical, risk level first (250). As described herein, the computing device may use other criteria to rank patients having the same risk level. The computing device user interface then presents the list of the ranked patients and each respective risk level (252). As long as no patient action is requested by the user ("NO" branch of block 254), the user interface continues to present the list of ranked patients (252). If a patient action has been requested by the user ("YES" branch of block 254), then the computing device performs the requested action to treat the patient (256). This action may be scheduling a clinic visit, ordering medication, or even dispatching emergency personnel to treat the patient. These actions may be performed to prevent the respective patient from needing to be re-hospitalized due to heart failure. Early detection of heart failure risk may allow for changes in treatment to better manage heart failure progression. If the user requests to view the list again ("YES" branch of block 258), the user interface again presents the list to the user (252). If the user does not wish to view the list again ("NO" branch of block 258), the user interface exists the list (260).

In other examples, the user may interact with the user interface to conduct further activities. For example, the external computing device may be capable of retrieving and presenting higher resolution diagnostic information (e.g., the patient metric data of each listed patient), calling the patient, programming therapy parameters of the remote IMD, adjusting metric instructions or metric-specific thresholds, or even modifying the rules for generating the heart failure risk levels or transmitting the risk level alerts to the external computing device.

EXAMPLE

The techniques described herein for generating heart failure risk levels (e.g., a type of lower resolution diagnostic information) were applied in a review of several studies to evaluate for the ability of the generated heart failure risk levels to predict the likelihood that a patient would be re-hospitalized within 30 days for heart failure. Each patient was monitored with an Implantable Cardioverter Defibrillator (ICD) or Cardiac Resynchronization Therapy Defibrillator (CRT-D) devices, e.g., example IMDs, to provide daily measurements of several patient metrics for possible evaluation of heart failure foe each patient. The retrospective analysis evaluated the ability of the generated heart failure risk level to identify which patients are at risk for re-admission to a hospital within 30 days following a hospital discharge after a heart failure event. Only patients with CRT-D devices and at least 90 days of follow-up data were used in the following analysis that included 1,561 patients.

Hospitalization due to heart failure was used as the endpoint in the data analysis. Each cardiovascular hospitalization was carefully adjudicated for signs and symptoms of heart failure which included administration of intra-vascular (IV) or oral diuretic during the hospitalization. A heart failure hospitalization (HFH) group was formed from the evaluated patients, which included patients with at least one heart failure hospitalization and at least 30 days of follow-up data following discharge from the first heart failure hospitalization.

Five patient metrics investigated in this analysis included intra-thoracic impedance, patient activity, night heart rate, heart rate variability, and AF diagnostics. However, other patient metrics could have been evaluated in other examples. AF burden, ventricular rate during AF, and % CRT pacing were combined into AF diagnostics as they may be correlated with each other. Initially each of the patient metrics was evaluated in a univariate fashion to determine the ability of each metric to identify patients at risk for heart failure hospitalization. Criteria were then chosen to determine the metric states of each metric that would correlate to a "High", "Medium", and "Low" risk level. These patient metrics and associated metric states are described in Table 1. In other examples, different criteria may be used to stratify or otherwise determine the metric state of each metric appropriate for effectively identifying the risk level that each patient would be re-hospitalized within 30 days. A "High" metric state may signify the highest probability of identifying a HFH while meeting the criteria approximately 5-10% of the time. The "Medium" metric state signifies a lower risk than the "High" status but a higher risk than the "Low" status. The "Low" metric state signifies minimal risk for a 30-day re-admission to the hospital. However, the metric states are individual risks, not the overall heart failure risk level described later.

As shown in Table 1, the "High" metric state for intra-thoracic impedance is determined based on then cumulative difference between the reference and daily impedance in the previous seven day period. If the daily impedance stays below the reference for the entire period, then the detected impedance is an indicator for a high risk of re-admission. Days with high atrial fibrillation (AF) burden (greater than 6 hours per day) and with poor rate control (Ventricular rate is greater than 90 beats per minute (BPM)) or a loss of CRT pacing (percentage of ventricular pacing less than 90 BPM) was considered "High" evidence for risk of re-hospitalization. Although AF burden may be combined with the loss of CRT pacing or CRT percentage as a single metric, AF burden, CRT percentage, or loss of CRT pacing alone may be used as a single metric in other examples. Days with night heart rate greater than 80 BPM or days with a night heart rate (NHR) greater than or equal to the daytime heart rate (DHR) during the seven day period indicated "High" evidence for risk of re-hospitalization. Similarly, a trend in reducing heart rate variability (HRV) at or below 40 milliseconds (ms) during the seven day period was considered "High" evidence for risk of re-hospitalization. Similarly, a trend in reducing activity during the seven day period indicated "High" evidence for risk of re-hospitalization.

eters. This weighting was used because some patient metrics may have a higher impact of heart failure risk level than other metrics. Alternatively, a Bayesian Belief Network (BBN) model was also created to evaluate all the individual metric states for each patient metric and generate a probabilistic risk score for the heart failure risk level. A 6-node BBN model was created for the patient metrics with heart failure being the parent node and the five different patient metrics as child nodes. The basic assumption of the BBN model is that inadequately treated heart failure causes the patient metrics to change. Therefore, measuring the patient metrics may enable an estimation of the possibility that a heart failure event may reoccur. Also, the BBN model assumes that, in the absence of any information regarding the heart failure status, the patient metrics are independent of each other.

Table 1 provides one example of patient metrics and associated scores based on the values of each metric. In other examples, fewer or greater metrics may be used for the heuristic evaluation of the patient. In addition, the scores provided in Table 1 are examples and may be varied based on the number of metrics evaluated, the number of risk levels for each metric, patient history indicating importance of one or more metrics, or other reasons related to monitoring the patient.

Table 2 provides an alternative set of patient metrics and score weights than the metrics and scores provided in the

TABLE 1

| Patient Metric | Criteria | Metric State | Score Weight |
|---|---|---|---|
| Intrathoracic Impedance | ≥1 days Fluid Index ≥60 in 7 days AND Mean(Impedance-Reference) in 7 days <−5.5 Ohms | High | 4 |
| | Not "High" or "Low" | Medium | 2 |
| | Mean(Impedance-Reference) in 7 days >+1.0 and not "High" | Low | 0 |
| Activity | Activity Slope* in 7 days <−100 | High | 2 |
| | Not "High" or "Low" | Medium | 1 |
| | Activity Slope* in 7 days >0 AND not "High" | Low | 0 |
| Heart Rate Variability | ≥5 days with HRV ≤40 ms in last 7 days OR {HRV slope* <−40 AND ≥5 days with HRV≤40 ms} | High | 2 |
| | HRV slope* <−20 and not "High" | Medium | 1 |
| | Not "High" or "Medium" | Low | 0 |
| Night Heart Rate | ≥1 days with (DHR-NHR)<0 bpm AND ≥5 days with NHR≥80 min/day | High | 2 |
| | ≥1 days with NHR≥80 min/day AND not "High" | Medium | 1 |
| | Not "High" or "Medium" | Low | 0 |
| AF + RVR | ≥1 day with AF >6 hrs AND with VR-AF >90 bpm OR 1-6 days with AF >6 hrs AND ≥1 day with % VP <90% | High | 4 |
| | 1-6 days with AF >6 hrs AND ≥1 day with % VP <90% AND Not "High" | Medium | 2 |
| | Not "High" or "Medium" | Low | 0 |

*Slope measurements for HRV and Activity were performed by subtracting the values on day 1-2 from the values on day 6-7 in the window of 7 days post discharge.

A heuristic evaluation of the patient metrics was created by assigning a score to each of the metric states for each patient metric. Then, the five scores were added to determine the heart failure risk level. The scores assigned to each metric state for the patient metrics are shown in Table 1. The intra-thoracic impedance and AF+RVR parameters was weighted double that of the metric states of other paramexample of Table 1. For example, the patient metrics of Table 2 may be used when other metrics may not be available or when the patient metrics of Table 2 are those metrics identified as particularly indicative of a re-hospitalization risk. In this manner, a variety of different patient metrics, criteria, and score weights may be used to evaluate the risk of re-hospitalization for a particular patient.

TABLE 2

| Patient Metric | Criteria | Metric State | Score Weight |
|---|---|---|---|
| Intrathoracic Impedance | ≥1 days Fluid Index ≥60 in 7 days AND Mean(Impedance-Reference) in 7 days <−5.5 Ohms | High | 3 |
| | Mean(Impedance-Reference) in 7 days >+1.0 and not "High" | Medium | 1 |
| | Not "High" or "Medium" | Low | 0 |
| Night Heart Rate | ≥1 days with NHR≥80 bmp | High | 1 |
| | Not "High" | Low | 0 |
| AF + RVR | TWO or more of: ≥1 day with AF >6 hrs AND with VR-AF >90 bpm; 1-6 days with AF >6 hrs; ≥1 day with % VP <90% | High | 2 |
| | ONE of: ≥1 day with AF >6 hrs AND with VR-AF >90 bpm; 1-6 days with AF >6 hrs; ≥1 day with % VP <90% | Medium | 1 |
| | Not "High" or "Medium" | Low | 0 |

Figure 13:
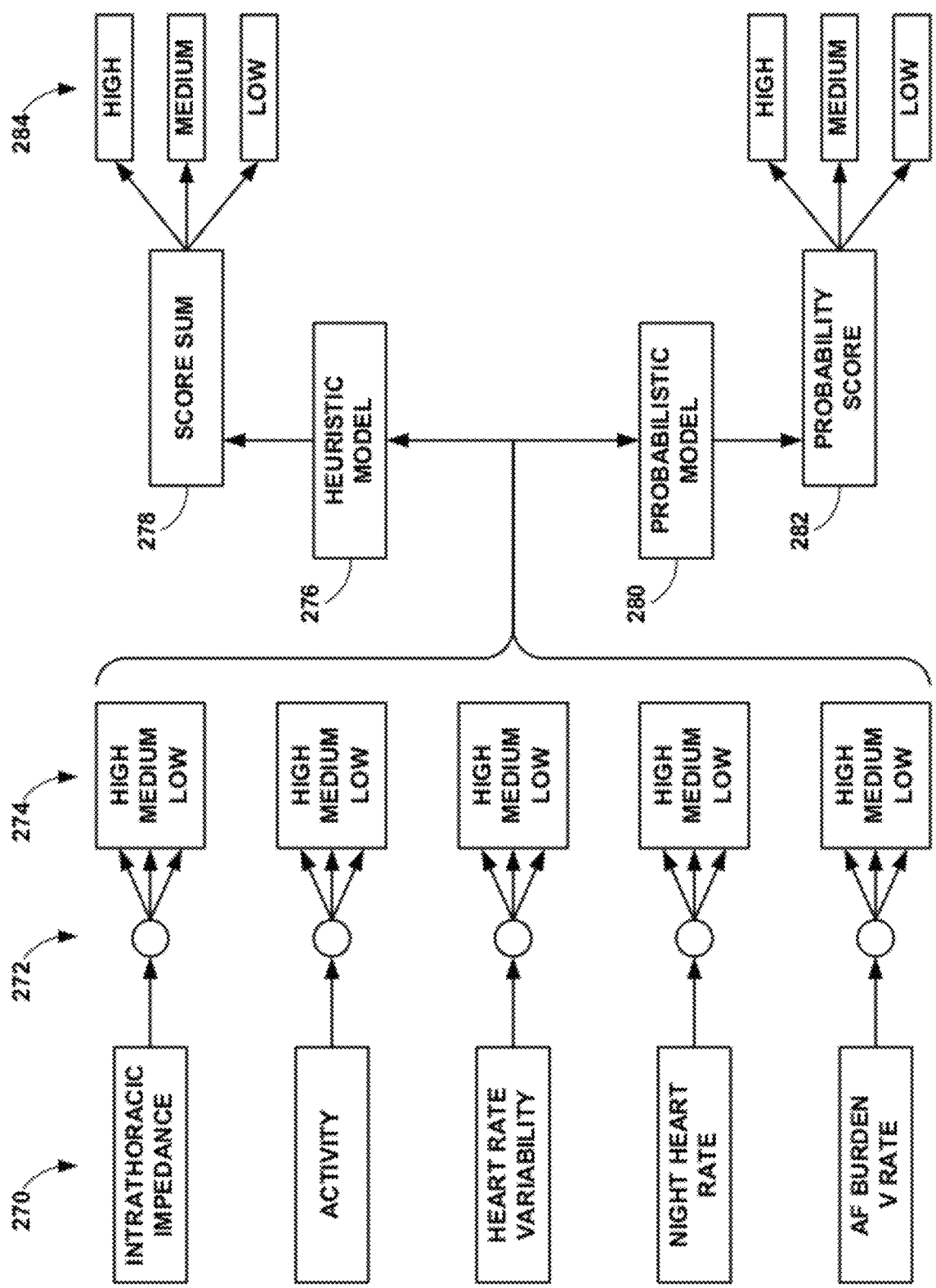
FIG. 13 is a flow diagram of example techniques for generating a heart failure risk level using an heuristic and/or a probabilistic model.

FIG. 13 is a flow diagram of example techniques for generating a heart failure risk level 284 using heuristic model 276 or probabilistic model 280. As shown in FIG. 13, each of the five patient metrics 270 is detected and analyzed using criteria 272. Criteria 272 may be criteria listed in Table 1 or other such metric-specific thresholds. Based on criteria 272, one of the metric states 274 for each patient metric is generated by the implantable device (e.g., IMD 16). Subsequently, the metric states are used to estimate the heart failure risk level using either model. Heuristic model 276 may use score sum 278 to add all of the metric state scores; the resulting sum is used to generate the heart failure risk level 284. Alternatively, probabilistic model 280 may use probability score 282 to identify the probability that the metric states indicate a certain heart failure risk level 284. Heart failure risk level 284 is categorized into three groups for analysis purposes. The thresholds for the different categories were chosen such that the "High" risk level is the top 15% of the scores, or more likely that the patient will be re-hospitalized. The "Low" category was chosen to represent all the diagnostic evaluation where the metric state for all the patient metrics was mostly "Low". The "Medium" category comprises of all other metric state combinations that did not get classified as either "High" or "Low".

At each heart failure hospitalization, the patient metrics were evaluated in the seven days post-hospitalization (e.g., post-discharge) to investigate whether a combined diagnostic criterion can identify the patients who are at higher risk of re-hospitalization for heart failure within the 30 day period following discharge. For patients with multiple heart failure hospitalizations, each hospitalization is considered for the purpose of the analysis if there was at least 30 days of follow-up data after discharge from that hospitalization. During the seven days following discharge after each hospitalization, the patient metrics were evaluated to classify the patient into the different heart failure risk levels. The patients in these risk level groups are then evaluated for heart failure hospitalization in the 30 days following discharge using the Anderson-Gill model, an extension of the Cox proportional hazards model that accounts for multiple evaluations in patients. A Generalized Estimating Equations (GEE) model is also used to estimate the probability of heart failure hospitalization in the next 30 days for each risk level group.

The results for each metric state are shown in Table 3. These results were derived from a heart failure hospitalization group comprising of a total of 254 heart failure hospitalizations in 166 patients. The results show that the "High" metric state during seven days post discharge for impedance, AF+RVR, and night heart rate identifies patients who were at a significantly higher risk for a 30 day re-admission due to heart failure.

TABLE 3

| Patient Metric | Metric State | Number of HF hospitalizations (%) | Number of 30-day readmission (%) |
|---|---|---|---|
| Impedance | High | 27 (11%) | 9 (33.3%) |
| | Medium | 129 (53%) | 18 (14.0%) |
| | Low | 88 (36%) | 4 (4.5%) |
| AF + RVR | High | 14 (6%) | 6 (42.9%) |
| | Medium | 45 (18%) | 11 (24.4%) |
| | Low | 195 (77%) | 17 (8.7%) |
| Night Heart Rate | High | 30 (13%) | 9 (30.0%) |
| | Medium | 68 (29%) | 11 (16.2%) |
| | Low | 139 (59%) | 12 (8.6%) |
| Activity | High | 27 (11%) | 7 (25.9%) |
| | Medium | 70 (28%) | 10 (14.3%) |
| | Low | 157 (62%) | 17 (10.8%) |
| Heart Rate Variability | High | 27 (16%) | 7 (25.9%) |
| | Medium | 27 (16%) | 4 (14.8%) |
| | Low | 114 (68%) | 11 (9.6%) |

The categorization of the heuristic model of patient metrics, by adding the scores assigned for each metric state during the seven day evaluation period, yielded three groups as shown in Table 4. A score sum of 0-2 indicates low evidence from the patient metrics that re-hospitalization due to heart failure is likely, whereas a score sum of greater than 6 indicates high evidence from patient metrics that re-hospitalization due to heart failure is likely. The cut-off for the low evidence group was chosen such that the metric states from all patient metrics is mostly "low". The cut-off for the high evidence group was chosen such that the high risk group included the top 15% of the sum scores. Based on the results, patients in the high risk group are almost 17 times more likely to be re-hospitalized within 30 days for heart failure than those patients included in the low risk group.

TABLE 4

| Score Sum Groups | Number of HF hospitalizations (%) | Number of 30-day readmission (%) | HR (95% CI) | p-value |
|---|---|---|---|---|
| 0-2 | 107 (42%) | 3 (2.8%) | Reference Group | |
| 3-5 | 108 (43%) | 16 (14.8%) | 5.59 (1.66-18.91) | 0.006 |
| 6-14 | 39 (15%) | 15 (38.5%) | 16.76 (4.92-57.08) | <0.001 |

Figure 14:
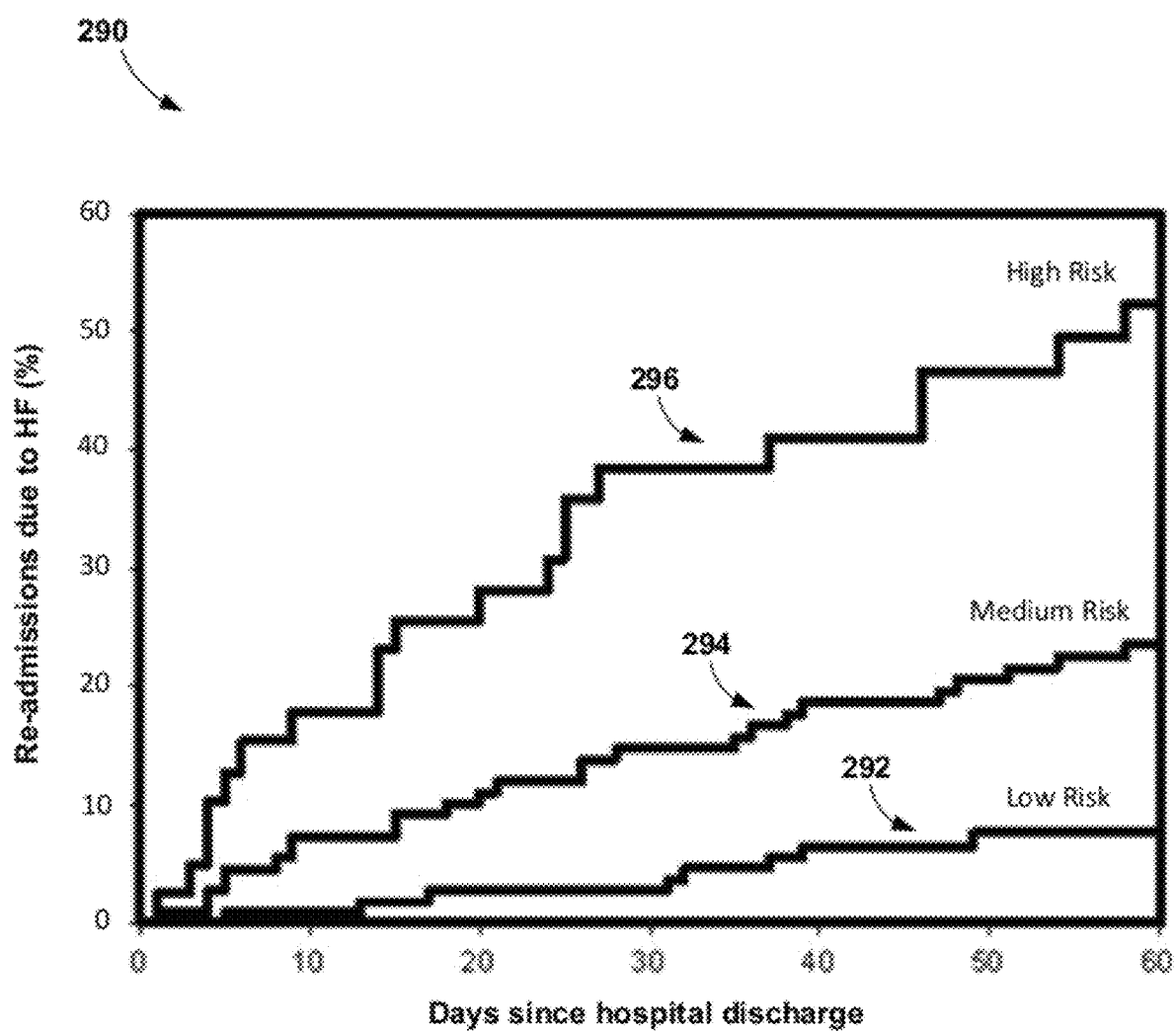
FIG. 14 is a graph of example re-hospitalization rates based on a generated risk level using a heuristic model.

FIG. 14 includes graph 290 of example re-hospitalization rates based on a generated risk level using heuristic model 276. Graph 290 was generated as a Kaplan Meier curve for incidence of re-hospitalization due to heart failure. As shown in FIG. 14, graph 290 provides low risk rate 292, medium risk rate 294, and high risk rate 296 over time. In other words, graph 290 indicates the percentage of patients with each risk level that were re-admitted to the hospital a certain number of days from the last hospital discharge. Low risk rate 292 includes patients with a low risk level, medium risk rate 294 includes patients with a medium risk level, and high risk rate 296 includes patients with a high risk level. The risk levels were described above with respect to the sum score. In other examples, similar risk rates may be seen if low risk level patients had no patient metrics exceeding the respective specific metric threshold, medium risk level patients had one patient metric exceeding the respective specific metric threshold, and high risk level patients had two or more patient metrics exceeding the respective specific metric thresholds.

Generally, patients with more severe risk levels had a higher re-admission rate to the hospital than patients with lower risk levels. For example, high risk rate 296 indicates that patients with a high risk level had an approximately 52% re-hospitalization rate after 60 days post-discharge compared with an approximately 8% re-hospitalization rate after 60 days post-discharge for low risk level patients. Since higher risk levels may indicate a higher probability that a particular patient may be re-hospitalized, a clinician may adjust treatment or otherwise help a patient with a more severe risk level to prevent future hospitalization due to heart failure.

The categorization of the probabilistic model of patient metrics, using the Bayesian Belief Network model for the metric state of each patient metric during the seven day diagnostic evaluation, yielded three groups as shown in Table 5. A probability score of less than 5% indicates a low risk level from the patient metrics, whereas a probability score of greater than 25% indicates a high risk level from the patient metrics. The cut-off for the low risk level group was chosen such that the metric state from all patient metrics was mostly "low". The cut-off for the high risk level group was chosen such that the high risk level group included the top 15% of the probability scores. According to the probabilistic model, patients in the high risk level group is 26 times more likely to be re-hospitalized within 30 days of discharge for heart failure than patients in the low risk level group.

TABLE 5

| Probability Score Groups | Number of HF hospitalizations (%) | Number of 30-day readmission (%) | HR (95% CI) | p-value |
|---|---|---|---|---|
| <5% | 111 (44%) | 2 (1.8%) | Reference Group | |
| 5%-25% | 106 (42%) | 18 (17.0%) | 10.11 (2.36-43.22) | 0.002 |
| ≥25% | 37 (15%) | 14 (37.8%) | 26.12 (6.32-107.90) | <0.001 |

Figure 15:
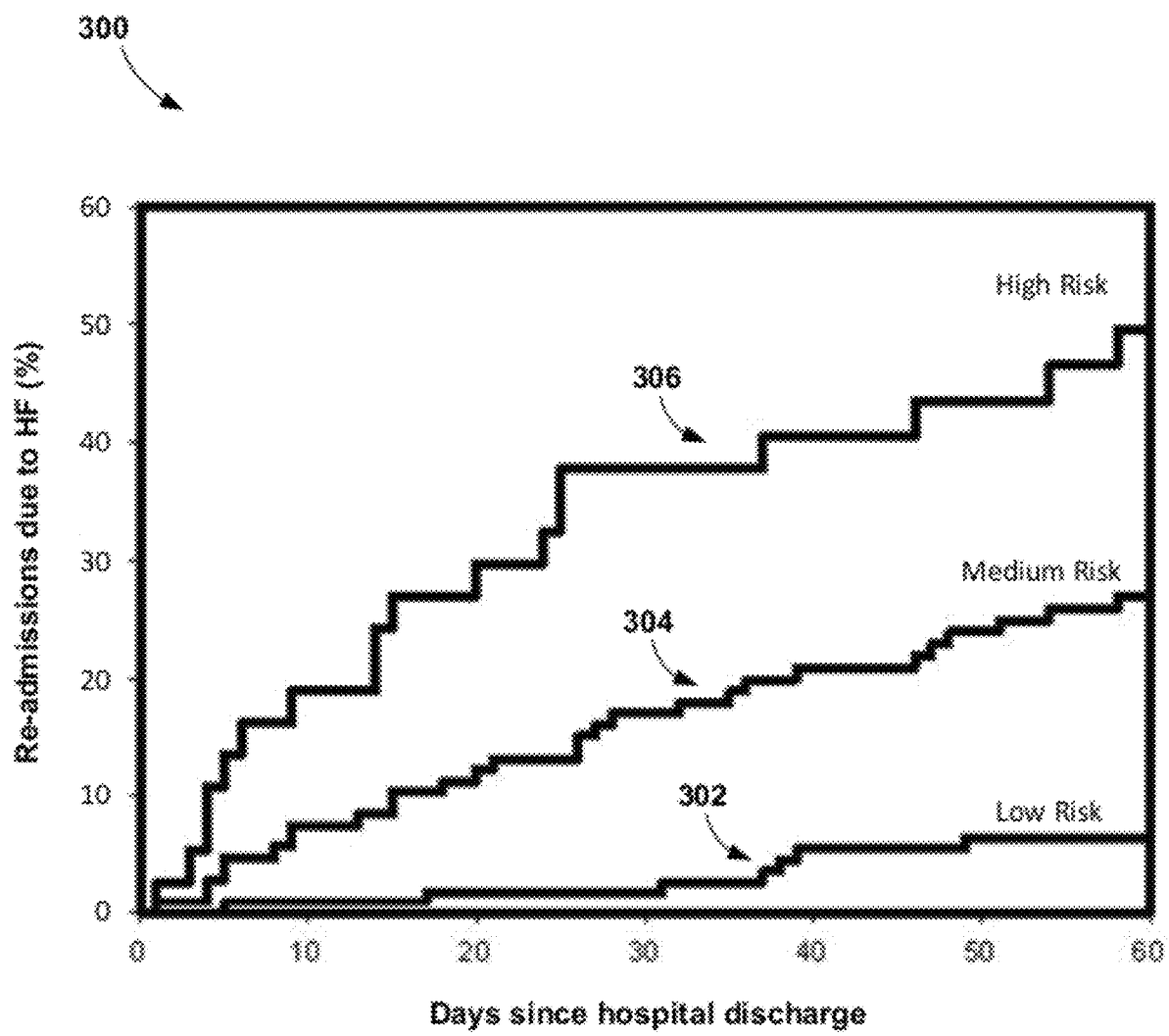
FIG. 15 is a graph of example re-hospitalization rates based on a generated risk level using a probabilistic model.

FIG. 15 includes graph 300 of example re-hospitalization rates based on a generated risk level using a probabilistic model. Graph 300 was generated as a Kaplan Meier curve for incidence of re-hospitalization due to heart failure, similar to graph 290 of FIG. 14. As shown in FIG. 15, graph 300 provides low risk rate 302, medium risk rate 304, and high risk rate 306 over time. In other words, graph 300 indicates the percentage of patients with each risk level that were re-admitted to the hospital a certain number of days from the last hospital discharge. Low risk rate 302 includes patients with a low risk level, medium risk rate 304 includes patients with a medium risk level, and high risk rate 306 includes patients with a high risk level. This risk rates correspond to the data presented in Table 5. The risk levels were described above with respect to the probability score generated by the BBN model.

Generally, patients with more severe risk levels had a higher re-admission rate to the hospital than patients with lower risk levels. For example, high risk rate 306 indicates that patients with a high risk level had an approximately 50% re-hospitalization rate after 60 days post-discharge compared with an approximately 6% re-hospitalization rate after 60 days post-discharge for low risk level patients. Since higher risk levels may indicate a higher probability that a particular patient may be re-hospitalized, a clinician may adjust treatment or otherwise help a patient with a more severe risk level to prevent future hospitalization due to heart failure.

The techniques described herein allow an IMD to transmit diagnostic information in higher or lower resolution based on what is needed to treat the patient. Before hospitalization, the IMD may transmit patient metric information to a clinician regarding to aid the clinician in making a determination about patient admission to the hospital. In this manner, the patient metrics stored in the IMD may help to determine whether the patient condition is due to possible heart failure, for example. During a hospitalization period, the IMD may transmit higher resolution diagnostic information to the clinician. This higher resolution diagnostic information may present values of patient metrics as an indication of patient status. Therefore, the clinician may benefit from additional information, e.g., thoracic impedance, indicative of heart failure improvements or worsening. Post-hospitalization, the IMD may transmit lower resolution diagnostic information indicative of the risk that the patient may be re-hospitalized. In other words, the risk level may identify those patients at a higher risk of re-hospitalization. This lower resolution diagnostic information may be remotely transmitted to allow for continued patient monitoring outside of the hospital or clinic. Upon receiving an elevated risk of re-hospitalization from the IMD, a clinician may alter the treatment of the respective patient. These techniques may aid in earlier treatment, minimized patient complications and hospital stays, and a higher quality of life for those patients at risk of heart failure.

In one example, a method may include storing a plurality of automatically detected patient metrics within an implantable medical device of a patient, transmitting higher resolution diagnostic information during a hospitalization period of the patient, wherein the higher resolution diagnostic information is based on at least one of the plurality of patient metrics and indicative of heart failure, and transmitting lower resolution diagnostic information during a post-hospitalization period of the patient, wherein the lower resolution diagnostic information is based on the plurality of patient metrics and indicative of a risk of re-hospitalization due to heart failure. The higher resolution diagnostic information and/or the lower resolution diagnostic information may be transmitted to an external device used by a user (e.g., a clinician).

The method may, in some examples, also include transmitting the lower resolution diagnostic information to the user prior to the hospitalization period or switching to transmitting higher resolution diagnostic information to the user during the post-hospitalization period upon one of the plurality of automatically detected patient metrics exceeding a respective one of a plurality of metric-specific thresholds. In other examples, storing the plurality of automatically detected patient metrics may comprise storing automatically detected patient metrics with a dynamic data storage rate, and the dynamic storage rate is higher for the higher resolution diagnostic information and lower for the lower resolution diagnostic information. In addition, the method may include transmitting at least one of the plurality of automatically detected patient metrics to the user in response to an interrogation request before entering the hospitalization period or remotely interrogating the implantable medical device during the post-hospitalization period to initiate transmission of lower resolution diagnostic information detected over a predetermined period.

In another example, an implantable medical device may include a memory configured to store a plurality of automatically detected patient metrics, a metric detection module configured to generate higher resolution diagnostic information based on at least one of the plurality of patient metrics and indicative of heart failure and generate lower resolution diagnostic information based on the plurality of patient metrics and indicative of a potential re-hospitalization period due to heart failure, and a telemetry module configured to transmit the higher resolution diagnostic information during a hospitalization period of the patient and lower resolution diagnostic information during a post-hospitalization period of the patient. The higher resolution diagnostic information and/or the lower resolution diagnostic information may be transmitted by the telemetry module to an external device used by a user (e.g., a clinician).

The metric detection module may generate a heart failure risk level with a Bayesian Belief Network based on the plurality of automatically generated patient metrics, wherein the lower resolution diagnostic information comprises the heart failure risk level. In some examples, the telemetry module transmits at least one of the plurality of automatically detected patient metrics to a user in response to receiving an interrogation request before entering the hospitalization period.

In another example, a system may include means for storing a plurality of automatically detected patient metrics within an implantable medical device of a patient, and means for transmitting information, wherein the means for transmitting information comprises means for transmitting higher resolution diagnostic information during a hospitalization period of the patient, the higher resolution diagnostic information is based on at least one of the plurality of patient metrics and indicative of heart failure, the means for transmitting information comprises means for transmitting lower resolution diagnostic information during a post-hospitalization period of the patient, and the lower resolution diagnostic information is based on the plurality of patient metrics and indicative of a potential re-hospitalization period due to heart failure. The higher resolution diagnostic information and/or the lower resolution diagnostic information may be transmitted, by the means for transmitting information, to an external device used by a user (e.g., a clinician).

In another example, a method may include storing a plurality of automatically detected patient metrics within an implantable medical device of a patient, generating lower resolution diagnostic information, wherein the lower resolution diagnostic information is based on the plurality of patient metrics and indicative of a risk of hospitalization due to heart failure, and triggering generation of higher resolution diagnostic information in response to the risk of hospitalization exceeding a predetermined risk level, wherein the higher resolution diagnostic information is based on at least one of the plurality of patient metrics and indicative of heart failure.

In another example, an implantable medical device may include a memory configured to store a plurality of automatically detected patient metrics, a metric detection module configured to generate lower resolution diagnostic information based on the plurality of patient metrics and indicative of a potential re-hospitalization period due to heart failure and trigger generation of higher resolution diagnostic information in response to the risk of hospitalization exceeding a predetermined risk level, wherein the higher resolution diagnostic information is based on at least one of the plurality of patient metrics and indicative of heart failure, and a telemetry module configured to transmit at least one of the lower resolution diagnostic information and the higher resolution diagnostic information.

Various examples have been described that include detecting and storing patient metrics and transmitting high and lower resolution diagnostic data from an IMD. These examples include techniques for identifying patients with an elevated risk of being re-hospitalized due to heart failure. In addition, an alert of patient risk levels may be remotely delivered to a healthcare professional from multiple different patients for triage and earlier diagnosis and treatment of heart failure before re-hospitalization. Any combination of detection and notification of heart failure risk level is contemplated. These and other examples are within the scope of the following claims.

The invention claimed is:

1. A method comprising:
    storing, by an implantable medical device, a plurality of automatically detected patient metrics within the implantable medical device of a patient;
    transmitting, by the implantable medical device, higher resolution diagnostic information during a hospitalization period of the patient, wherein the higher resolution diagnostic information is based on at least one of the plurality of patient metrics and indicative of heart failure; and
    transmitting, by the implantable medical device, lower resolution diagnostic information during a post-hospitalization period of the patient, wherein the lower resolution diagnostic information is based on the plurality of patient metrics and indicative of a risk of re-hospitalization due to heart failure, and wherein the lower resolution diagnostic information comprises a first resolution lower than a second resolution of the higher resolution diagnostic information.

2. The method of claim 1, wherein the higher resolution diagnostic information comprises values of the at least one patient metric detected at least one of:
    once every two hours; or
    on-demand during the hospitalization period.

3. The method of claim 2, wherein the at least one patient metric comprises at least one of an intrathoracic impedance, a thoracic fluid level, an atrial fibrillation duration after cardioversion therapy, a heart rate variability, a stabilization of ventricular rate during persistent atrial fibrillation, a stabilization of night heart rate, and a cardiac resynchronization therapy percentage.

4. The method of claim 1, further comprising:
comparing each of the plurality of automatically detected patient metrics to a respective one of a plurality of metric-specific thresholds; and
automatically generating, by the implantable medical device, a heart failure risk level based on the comparison, wherein the heart failure risk level is indicative of the risk of re-hospitalization for heart failure, and wherein the lower resolution diagnostic information comprises the heart failure risk level.

5. The method of claim 4, wherein the heart failure risk level is based on a predetermined number of the plurality of automatically detected patient metrics that each exceed the respective one of the plurality of metric-specific thresholds.

6. The method of claim 5, wherein:
the heart failure risk level indicates a high risk of re-hospitalization when the predetermined number of the plurality of automatically detected patient metrics is two or more automatically detected patient metrics each exceeding the respective one of the plurality of metric-specific thresholds;
the heart failure risk level indicates a medium risk of re-hospitalization when the predetermined number of the plurality of automatically detected patient metrics is one automatically detected patient metric exceeding the respective one of the plurality of metric-specific thresholds;
the heart failure risk level indicates a low risk of re-hospitalization when the predetermined number of the plurality of automatically detected patient metrics is zero automatically detected patient metrics exceeding the respective one of the plurality of metric-specific thresholds; and
the plurality of automatically detected patient metrics includes at least eight different automatically detected patient metrics.

7. The method of claim 5, wherein:
the plurality of automatically detected patient metrics comprises at least two of a thoracic impedance, an atrial fibrillation duration, a ventricular contraction rate during atrial fibrillation, a patient activity, a nighttime heart rate, a heart rate variability, a cardiac resynchronization therapy percentage, a ventricular pacing percentage, and an electrical shock event; and
the plurality of metric-specific thresholds comprise at least two of an atrial fibrillation duration threshold of approximately 6 hours, a ventricular contraction rate threshold approximately equal to 90 beats per minute for 24 hours, a patient activity threshold approximately equal to 1 hour per day for seven consecutive days, a nighttime heart rate threshold of approximately 85 beats per minute for seven consecutive days, a heart rate variability threshold of approximately 40 milliseconds for seven consecutive days, a cardiac resynchronization therapy percentage threshold of 90 percent for five of seven consecutive days, and an electrical shock threshold of 1 electrical shock.

8. The method of claim 1, further comprising generating a heart failure risk level with a Bayesian Belief Network based on the plurality of automatically generated patient metrics, wherein the lower resolution diagnostic information comprises the heart failure risk level.

9. The method of claim 1, further comprising:
remotely interrogating a plurality of implantable medical devices during the post-hospitalization period for a plurality of patients to initiate transmission of lower resolution diagnostic information detected over a predetermined period, wherein each of the plurality of implantable medical devices is implanted in a different one of the plurality of patients;
transmitting lower resolution diagnostic information from each of the implantable medical devices; and
presenting the transmitted lower resolution diagnostic information arranged according to a re-hospitalization risk of each of the plurality of patients.

10. The method of claim 1, further comprising:
determining, by the implantable medical device, that the patient has been hospitalized and higher resolution diagnostic information is to be transmitted;
responsive to determining that the patient has been hospitalized, transmitting, by the implantable medical device, the higher resolution diagnostic information;
determining, by the implantable medical device, that the patient has entered the post-hospitalization period; and
responsive to determining that the patient has entered the post-hospitalization period, transmitting, by the implantable medical device, the lower resolution diagnostic information during the post-hospitalization period.

11. The method of claim 1, wherein:
the higher resolution diagnostic information comprises respective values of the plurality of automatically detected patient metrics; and
the lower resolution diagnostic information comprises a heart failure risk level instead of the respective values of the plurality of automatically detected patient metrics, the heart failure risk level generated based on a comparison of the respective values of the plurality of automatically detected patient metrics to respective metric-specific thresholds.

12. An implantable medical device comprising:
a memory configured to store a plurality of automatically detected patient metrics;
metric detection circuitry configured to generate higher resolution diagnostic information based on at least one of the plurality of patient metrics and indicative of heart failure and generate lower resolution diagnostic information based on the plurality of patient metrics and indicative of a potential re-hospitalization period due to heart failure, wherein the lower resolution diagnostic information comprises a first resolution lower than a second resolution of the higher resolution diagnostic information; and
telemetry circuitry configured to transmit the higher resolution diagnostic information during a hospitalization period of the patient and lower resolution diagnostic information during a post-hospitalization period of the patient.

13. The implantable medical device of claim 12, wherein the metric detection circuitry is configured to generate the higher resolution diagnostic information with values of the at least one patient metric detected at least one of once every two hours or on-demand during the hospitalization period.

14. The implantable medical device of claim 12, wherein the at least one patient metric comprises at least one of an intrathoracic impedance, a thoracic fluid level, an atrial fibrillation duration after cardioversion therapy, a heart rate variability, a stabilization of ventricular rate during persistent atrial fibrillation, a stabilization of night heart rate, and a cardiac resynchronization therapy percentage.

15. The implantable medical device of claim 12, wherein the metric detection circuitry is configured to:
- compare each of the plurality of automatically detected patient metrics to a respective one of a plurality of metric-specific thresholds; and
- automatically generate a heart failure risk level based on the comparison, wherein the heart failure risk level is indicative of the risk of re-hospitalization for heart failure, and wherein the lower resolution diagnostic information comprises the heart failure risk level.

16. The implantable medical device of claim 15, wherein the heart failure risk level is based on a predetermined number of the plurality of automatically detected patient metrics that each exceed the respective one of the plurality of metric-specific thresholds.

17. The implantable medical device of claim 16, wherein:
- the heart failure risk level indicates a high risk of re-hospitalization when the predetermined number of the plurality of automatically detected patient metrics is two or more automatically detected patient metrics each exceeding the respective one of the plurality of metric-specific thresholds;
- the heart failure risk level indicates a medium risk of re-hospitalization when the predetermined number of the plurality of automatically detected patient metrics is one automatically detected patient metrics exceeding the respective one of the plurality of metric-specific thresholds;
- the heart failure risk level indicates a low risk of re-hospitalization when the predetermined number of the plurality of automatically detected patient metrics is zero automatically detected patient metrics exceeding the respective one of the plurality of metric-specific thresholds; and
- the plurality of automatically detected patient metrics includes at least eight different automatically detected patient metrics.

18. The implantable medical device of claim 12, wherein the telemetry circuitry is configured to transmit the lower resolution diagnostic information to an external device prior to the hospitalization period.

19. The implantable medical device of claim 12, wherein the telemetry circuitry is configured to switch to transmitting higher resolution diagnostic information during the post-hospitalization period in response to the metric detection circuitry determining one of the plurality of automatically detected patient metrics exceeds a respective one of a plurality of metric-specific thresholds.

20. The implantable medical device of claim 12, wherein the metric detection circuitry is configured to store the plurality of automatically detected patient metrics in the memory with a dynamic data storage rate, and wherein the dynamic storage rate is higher for the higher resolution diagnostic information and lower for the lower resolution diagnostic information.

21. The implantable medical device of claim 12, wherein the telemetry circuitry is configured to initiate transmission of lower resolution diagnostic information detected over a predetermined period in response to receiving a remote interrogation request during the post-hospitalization period.

22. A system comprising:
- means for storing a plurality of automatically detected patient metrics within an implantable medical device of a patient; and
- means for transmitting, by the implantable medical device, information, wherein:
  - the means for transmitting information comprises means for transmitting higher resolution diagnostic information during a hospitalization period of the patient;
  - the higher resolution diagnostic information is based on at least one of the plurality of patient metrics and indicative of heart failure;
  - the means for transmitting information comprises means for transmitting lower resolution diagnostic information during a post-hospitalization period of the patient; and
  - the lower resolution diagnostic information is based on the plurality of patient metrics and indicative of a potential re-hospitalization period due to heart failure, and wherein the lower resolution diagnostic information comprises a first resolution lower than a second resolution of the higher resolution diagnostic information.

* * * * *